(12) United States Patent
Centen et al.

(10) Patent No.: US 11,696,715 B2
(45) Date of Patent: Jul. 11, 2023

(54) CARDIOVASCULAR SIGNAL ACQUISITION, FUSION, AND NOISE MITIGATION

(71) Applicant: Bodyport Inc., San Francisco, CA (US)

(72) Inventors: Corey James Centen, San Francisco, CA (US); Sarah Ann Smith, San Francisco, CA (US); Sarin Patel, Union City, CA (US)

(73) Assignee: Bodyport Inc., San Francisco, CA (US)

( * ) Notice: Subject to any disclaimer, the term of this patent is extended or adjusted under 35 U.S.C. 154(b) by 1161 days.

(21) Appl. No.: 16/163,343

(22) Filed: Oct. 17, 2018

(65) Prior Publication Data

US 2019/0046064 A1 Feb. 14, 2019

Related U.S. Application Data

(63) Continuation-in-part of application No. 15/743,154, filed as application No. PCT/CA2015/051120 on Nov. 2, 2015.

(Continued)

(51) Int. Cl.
*A61B 5/282* (2021.01)
*A61B 5/00* (2006.01)
(Continued)

(52) U.S. Cl.
CPC ............ *A61B 5/282* (2021.01); *A61B 5/0535* (2013.01); *A61B 5/1102* (2013.01); *A61B 5/318* (2021.01);
(Continued)

(58) Field of Classification Search
CPC ... A61B 5/0205; A61B 5/0245; A61B 5/0531; A61B 5/0535; A61B 5/0537; A61B 5/26;
(Continued)

(56) References Cited

U.S. PATENT DOCUMENTS 5,211,177 A 5/1993 Chesney et al.
5,410,471 A 4/1995 Alyfuku et al.
(Continued)

FOREIGN PATENT DOCUMENTS

CA 2605239 A1 11/2006
CA 2882453 A1 3/2014
(Continued)

OTHER PUBLICATIONS

Gonzalez-Landaeta, Rafael & Casas, Oscar & Pallas-Areny, Ramon. (2008). Heart Rate Detection From Plantar Bioimpedance Measurements. IEEE transactions on bio-medical engineering. 55. 1163-7. 10.1109/TBME.2007.906516. (Year: 2008).*

(Continued)

*Primary Examiner* — Tse W Chen
*Assistant Examiner* — Alice Ling Zou
(74) *Attorney, Agent, or Firm* — Fenwick & West LLP

(57) ABSTRACT

A device including an array of electrodes generates one or more electrical signals from a user, extracts one or more noise signals, and generates one or more de-noised electrical signals upon processing the electrical signal(s) with the noise signal(s). The array of electrodes is coupled to a surface of the device, where the device also includes force sensors in mechanical communication with the surface for detecting user weight and other forces. The device can be configured to generate electrical signals from different subportions of the array of electrodes and to extract noise signals from different subportions of the array of electrodes, where the subportion(s) for electrical signal generation may or may not overlap with the subportion(s) of electrodes for noise signal extraction.

16 Claims, 25 Drawing Sheets

Related U.S. Application Data

(60) Provisional application No. 62/191,318, filed on Jul. 10, 2015.

(51) Int. Cl.

| | |
|---|---|
| *A61B 5/0535* | (2021.01) |
| *A61B 5/318* | (2021.01) |
| *A61B 5/11* | (2006.01) |
| *A61B 5/0537* | (2021.01) |
| *A61B 5/024* | (2006.01) |
| *A61B 5/0245* | (2006.01) |
| *A61B 5/01* | (2006.01) |
| *A61B 5/366* | (2021.01) |

(52) U.S. Cl.
CPC .......... *A61B 5/6829* (2013.01); *A61B 5/7203* (2013.01); *A61B 5/725* (2013.01); *A61B 5/7221* (2013.01); *A61B 5/7275* (2013.01); *A61B 5/01* (2013.01); *A61B 5/0245* (2013.01); *A61B 5/02405* (2013.01); *A61B 5/02444* (2013.01); *A61B 5/0537* (2013.01); *A61B 5/11* (2013.01); *A61B 5/366* (2021.01); *A61B 5/4869* (2013.01); *A61B 5/721* (2013.01); *A61B 5/7225* (2013.01); *A61B 5/7239* (2013.01); *A61B 5/7292* (2013.01)

(58) Field of Classification Search
CPC .............. A61B 5/28–282; A61B 5/301; A61B 5/304–305; A61B 5/308; A61B 5/318–319; A61B 5/327; A61B 5/346; A61B 5/35; A61B 5/6829; A61B 5/6887; A61B 5/6892; A61B 5/6898; A61B 5/7207–7214; A61B 5/7221; A61B 5/725; A61B 5/7278; A61B 5/25; A61B 5/268–27; A61B 5/276–277; A61B 5/30–305; A61B 5/316; A61B 5/321–322; A61B 5/33–333; A61B 5/7203–721

See application file for complete search history.

(56) References Cited

U.S. PATENT DOCUMENTS

| | | | |
|---|---|---|---|
| 5,704,365 A * | 1/1998 | Albrecht ................ | A61B 5/222 |
| | | | 600/515 |
| 5,817,031 A | 10/1998 | Masuo et al. | |
| 7,163,516 B1 | 1/2007 | Pagnacco et al. | |
| 7,395,104 B2 | 7/2008 | Mouradian et al. | |
| 8,007,450 B2 | 8/2011 | Williams | |
| 8,512,260 B2 | 8/2013 | Grudic et al. | |
| 8,535,247 B2 | 9/2013 | Williams | |
| 8,652,070 B2 | 2/2014 | Williams | |
| 8,652,071 B2 | 2/2014 | Williams | |
| 9,820,696 B1 | 11/2017 | Narasimhan | |
| 2002/0193689 A1 | 12/2002 | Bernstein et al. | |
| 2004/0251057 A1 | 12/2004 | Suzuki | |
| 2005/0039763 A1 | 2/2005 | Kraemer et al. | |
| 2005/0171451 A1 | 8/2005 | Yeo et al. | |
| 2005/0197549 A1 | 9/2005 | Baker | |
| 2006/0009710 A1 | 1/2006 | Bernstein | |
| 2006/0212484 A1 | 9/2006 | Chaffin et al. | |
| 2006/0287889 A1 | 12/2006 | Brown | |
| 2007/0276262 A1 | 11/2007 | Banet et al. | |
| 2008/0027341 A1 * | 1/2008 | Sackner ................ | A61B 5/318 |
| | | | 600/509 |
| 2008/0045804 A1 | 2/2008 | Williams | |
| 2008/0162183 A1 | 7/2008 | Sachanandani et al. | |
| 2008/0221404 A1 | 9/2008 | Tso | |
| 2008/0243026 A1 | 10/2008 | Tsuji | |
| 2009/0018453 A1 | 1/2009 | Banet et al. | |
| 2009/0204013 A1 | 8/2009 | Muhlsteff et al. | |
| 2010/0081946 A1 | 4/2010 | Garudadri et al. | |
| 2010/0094147 A1 | 4/2010 | Inan et al. | |
| 2010/0152623 A1 | 6/2010 | Williams | |
| 2010/0210921 A1 | 8/2010 | Park et al. | |
| 2011/0112443 A1 | 5/2011 | Williams | |
| 2011/0026401 A1 | 10/2011 | Williams | |
| 2012/0165691 A1 | 6/2012 | Ting et al. | |
| 2012/0253206 A1 * | 10/2012 | Fukuda ................ | A61B 5/053 |
| | | | 600/483 |
| 2013/0041235 A1 | 2/2013 | Rogers et al. | |
| 2013/0109946 A1 | 5/2013 | Shim et al. | |
| 2013/0211482 A1 | 8/2013 | Pipponen | |
| 2013/0296723 A1 | 11/2013 | Cho et al. | |
| 2013/0297217 A1 | 11/2013 | Bangera et al. | |
| 2013/0310700 A1 | 11/2013 | Wiard et al. | |
| 2014/0066798 A1 | 3/2014 | Albert | |
| 2014/0200469 A1 | 7/2014 | Bocko et al. | |
| 2014/0308930 A1 | 10/2014 | Tran | |
| 2014/0323824 A1 | 10/2014 | Addison et al. | |
| 2014/0330090 A1 | 11/2014 | Banet et al. | |
| 2014/0371635 A1 | 12/2014 | Shinar et al. | |
| 2015/0164351 A1 | 6/2015 | He et al. | |
| 2015/0257679 A1 | 9/2015 | Ross | |
| 2015/0260514 A1 | 9/2015 | Menelas et al. | |
| 2015/0359441 A1 | 12/2015 | Giovangrandi et al. | |
| 2015/0362360 A1 | 12/2015 | Kovacs et al. | |
| 2016/0081563 A1 | 3/2016 | Wiard et al. | |
| 2016/0345851 A1 * | 12/2016 | Brockway ............ | A61B 5/7203 |
| 2016/0374618 A1 * | 12/2016 | Giovangrandi ...... | A61B 5/0537 |
| | | | 600/393 |
| 2017/0014040 A1 | 1/2017 | Shim et al. | |
| 2017/0188845 A1 * | 7/2017 | Banet ..................... | A61B 5/352 |
| 2018/0199824 A1 | 7/2018 | Centen et al. | |

FOREIGN PATENT DOCUMENTS

| | | | | |
|---|---|---|---|---|
| CN | 101065752 A | 10/2007 | | |
| EP | 1257318 B1 | 12/2006 | | |
| JP | H03159881 A | 7/1991 | | |
| JP | 2002-112976 A | 4/2002 | | |
| JP | 2005279278 A | 10/2005 | | |
| JP | 2006231020 A | 9/2006 | | |
| JP | 3866943 B2 | 1/2007 | | |
| JP | 2013043095 A | 3/2013 | | |
| JP | 2013123451 A | 6/2013 | | |
| JP | 2014076117 A | 5/2014 | | |
| WO | WO 2002/013691 A1 | 2/2002 | | |
| WO | WO-2012136744 A1 * | 10/2012 | ........... | A61B 5/0408 |
| WO | WO 2013/017717 A2 | 2/2013 | | |
| WO | WO 2014/032181 A1 | 3/2014 | | |
| WO | WO 2015/195983 A1 | 12/2015 | | |
| WO | WO-2019134032 A1 * | 7/2019 | ........... | A61B 5/0205 |

OTHER PUBLICATIONS

Chen, Z. et al., "Noninvasive Monitoring of Blood Pressure Using Optical Ballistocardiography and Photoplethysmograph Approaches," 35th Annual International Conference of the IEEE EMBS, Jul. 2013, pp. 2425-2428.

Deb, S. et al., "Cuff-less Estimation of Blood Pressure using Pulse Transit Time and Pre-ejection Period," 2007 International Conference on Convergence Information Technology, Nov. 2007, pp. 941-944.

Díaz, D. H. et al., "Heart Rate Detection from Single-Foot Plantar Bioimpedance Measurements in a Weighing Scale," 32nd Annual International Conference of the IEEE EMBS, Aug. 2010, pp. 6489-6492.

Garrard, C. L. et al., "The Relationship of Alterations in Systolic Time Intervals to Ejection Fraction in Patients with Cardiac Disease," Circulation, 42(3), Sep. 1970, pp. 455-462.

Omron Healthcare, Inc., "Omron Instruction Manual Body Composition Monitor with Scale Model HBF-SOOCAN," 2009, pp. 1-44, [Online] Retrieved from the Internet <URL: https://www.omronhealthcare.ca/wp-content/uploads/hbf-500can7im7eng704142010.pdf>.

Pathway Medicine, "Breathing Cycle," Mar. 24, 2015, two pages, {online} Retrieved from the Internet Archive <URL: https://web.

(56) References Cited

OTHER PUBLICATIONS archive.org/web/20150324095850/http://www.pathwaymedicine.org/breathing-cycle>.

United States Office Action, U.S. Appl. No. 15/743,154, dated Aug. 18, 2021, 26 pages.

Khalil, S.F et al., "The Theory and Fundamentals of Bioimpedance Analysis in Clinical Status Monitoring and Diagnosis of Diseases," Sensors, vol. 14, Jun. 19, 2014, pp. 10895-10928.

United States Office Action, U.S. Appl. No. 15/743,154, dated Oct. 2, 2020, 20 pages.

PCT International Search Report, PCT Application No. PCT/CA2015/051120, dated Apr. 12, 2016, 17 pages.

United States Office Action, U.S. Appl. No. 16/163,354, dated Sep. 16, 2020, 14 pages.

United States Office Action, U.S. Appl. No. 16/163,354, dated Feb. 18, 2021, 17 pages.

Ashley, E. A. et al., "Chapter 3: Conquering the ECG," Cardiology Explained, London: Remedica, 2004, pp. 1-34.

Malmivuo, J. et al., "Section 25.3.1 Measurement of the Impedance of the Thorax," in Bioelectromagnetism—Principles and Applications of Bioelectric and Biomagnetic Fields, New York, NY, etc.: Oxford University Press, Jan. 1995, pp. 544-545.

PCT International Search Report and Written Opinion, PCT Application No. PCT/US2019/056162, dated Dec. 20, 2019, 13 pages.

Canadian Intellectual Property Office, Office Action, Canadian Patent Application No. 2,992,038, dated Aug. 5, 2022, 4 pages.

Canadian Intellectual Property Office, Office Action, Canadian Patent Application No. 3,116,846, dated Jun. 22, 2022, 2 pages.

European Patent Office, Extended European Search Report and Opinion, European Patent Application No. 19873432.9, dated Nov. 4, 2022, 12 pages.

Japan Patent Office, Office Action, Japanese Patent Application No. 2021-546193, dated May 24, 2022, dated 12 pages.

Gomez-Clapers, J. et al. "Multi-Signal Bathroom Scale to Assess Long-Term Trends in Cardiovascular Parameters," *Annual International Conference of the IEEE Engineering in Medicine and Biology Society*, Aug.-Sep. 2012, pp. 550-553.

Shin, J.H. et al. "Non-Constrained Monitoring of Systolic Blood Pressure on a Weighing Scale," *Physiological Measurement*, vol. 30, No. 7, Jun. 12, 2009, pp. 679-693.

United States Office Action, U.S. Appl. No. 15/743,154, dated Nov. 25, 2022, 27 pages.

United States Office Action, U.S. Appl. No. 16/163,349, dated Aug. 17, 2022, 54 pages.

United States Office Action, U.S. Appl. No. 15/743,154, dated Apr. 27, 2022, 29 pages.

United States Office Action, U.S. Appl. No. 16/163,343, dated Dec. 10, 2021, 19 pages.

\* cited by examiner

CARDIOVASCULAR SIGNAL ACQUISITION, FUSION, AND NOISE MITIGATION

CROSS REFERENCE TO RELATED APPLICATIONS

This application is a continuation-in-part of co-pending U.S. application Ser. No. 15/743,154, filed on Jan. 9, 2018, which is a National State Entry of International Application No. PCT/CA2015/051120, filed on Nov. 2, 2015, which claims the benefit of priority to U.S. Provisional Application No. 62/191,318, filed on Jul. 10, 2015, all of which are incorporated by reference herein in their entirety. This application is also related to U.S. patent application Ser. No. 16/163,349, filed on Oct. 17, 2018, and U.S. patent application Ser. No. 16/163,354, filed on Oct. 17, 2018, the contents of both are hereby incorporated by reference.

BACKGROUND

This disclosure relates generally to user cardiovascular disease monitoring, and more specifically to acquiring biometric signals relevant to cardiovascular health, fusing signals, and mitigating noise in the signal(s).

About 1 of 3 U.S. adults (over 70 million people) have high blood pressure, but only approximately half of these individuals their high blood pressure under control. High blood pressure is often called a "silent killer" because it typically produces no warning signs or symptoms, but is associated with increased risk factors for more serious conditions, such as heart disease and stroke. Frequent monitoring of blood pressure and other biometric parameters relevant to cardiovascular health can enable early detection of abnormal or deteriorating cardiovascular health states; however, currently available home-use devices (e.g., pneumatic cuffs) are not user-friendly, are uncomfortable, are difficult to use, and are not designed to promote regular use, in relation to adherence to a health-monitoring regimen. Even further, devices for consumer use are limited in the types of signals they can acquire and effectively process to generate composite features relevant to different cardiovascular health states.

SUMMARY

A device including an array of electrodes generates one or more electrical signals from a user, extracts one or more noise signals, and generates one or more de-noised electrical signals upon processing the electrical signal(s) with the noise signal(s). The array of electrodes is coupled to a surface of the device, where the device also includes force sensors in mechanical communication with the surface for detecting user weight and other forces. The device can be configured to generate electrical signals from different subportions of the array of electrodes and to extract noise signals from different subportions of the array of electrodes, where the subportion(s) for electrical signal generation may or may not overlap with the subportion(s) of electrodes for noise signal extraction.

Collectively, the electrical signal(s) and the force-associated signal(s) generated by sensors of the device are processed by a computing subsystem with electronics and architecture configured for sensor fusion and extraction of composite features indicative of cardiovascular health states. In one or more embodiments, the device generates electrocardiogram (ECG) signals, impedance plethysmogram (IPG) signals, ballistocardiogram (BCG) signals, and weight measurements through an interface with feet of a user. Computing subsystem components fuse the ECG, IPG, and BCG data to efficiently generate analyses of cardiovascular health of the user, in relation to various parameters related to temporal components of cardiac phases, force and volume-associated parameters, and other relevant parameters. The parameters are regularly collected and analyzed to monitor user cardiovascular health and trigger preventative health interventions.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

Figure 1A:
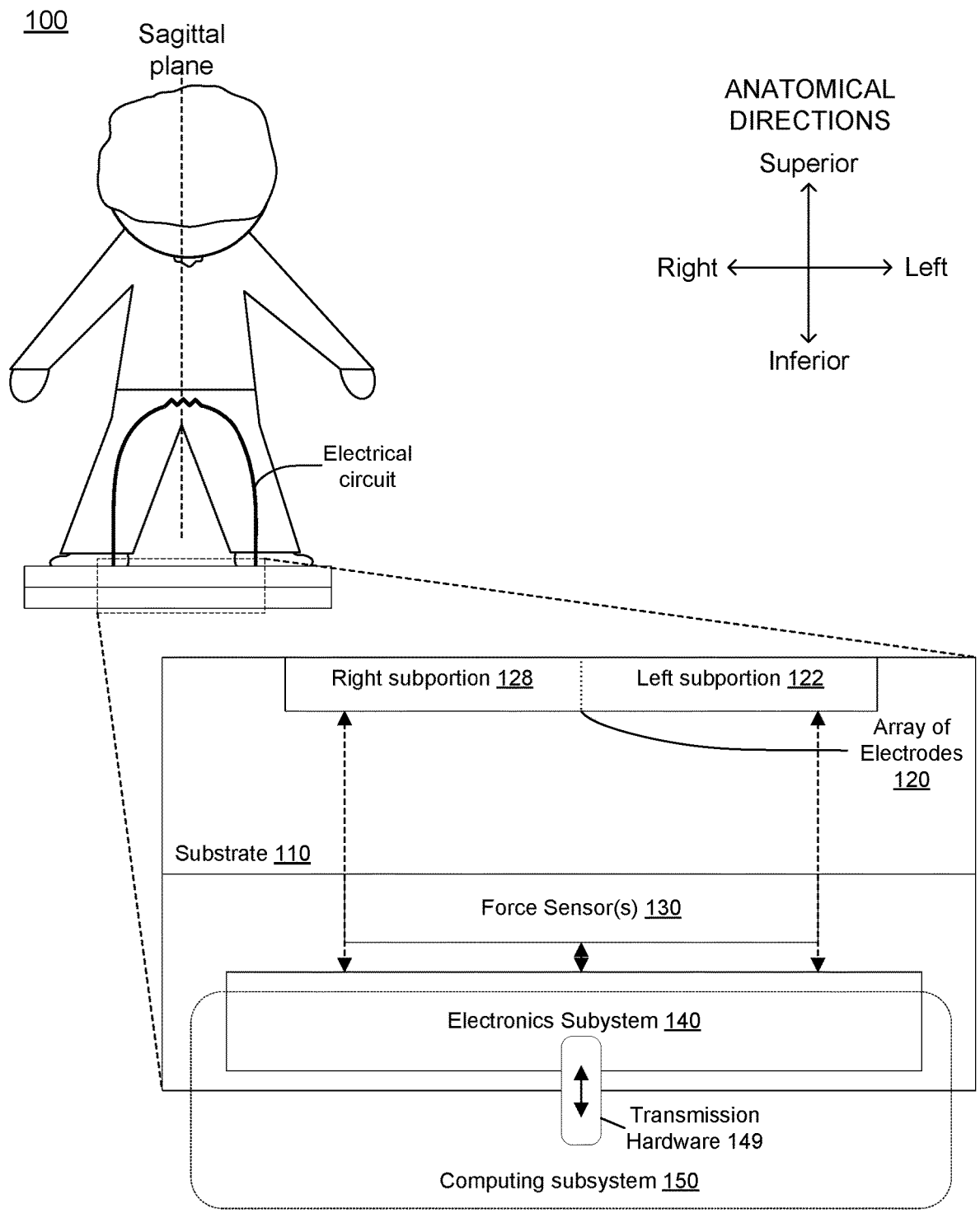
FIG. 1A depicts a schematic of a system for cardiovascular signal acquisition, fusion, and noise mitigation, in accordance with one or more embodiments.
Figure 1B:
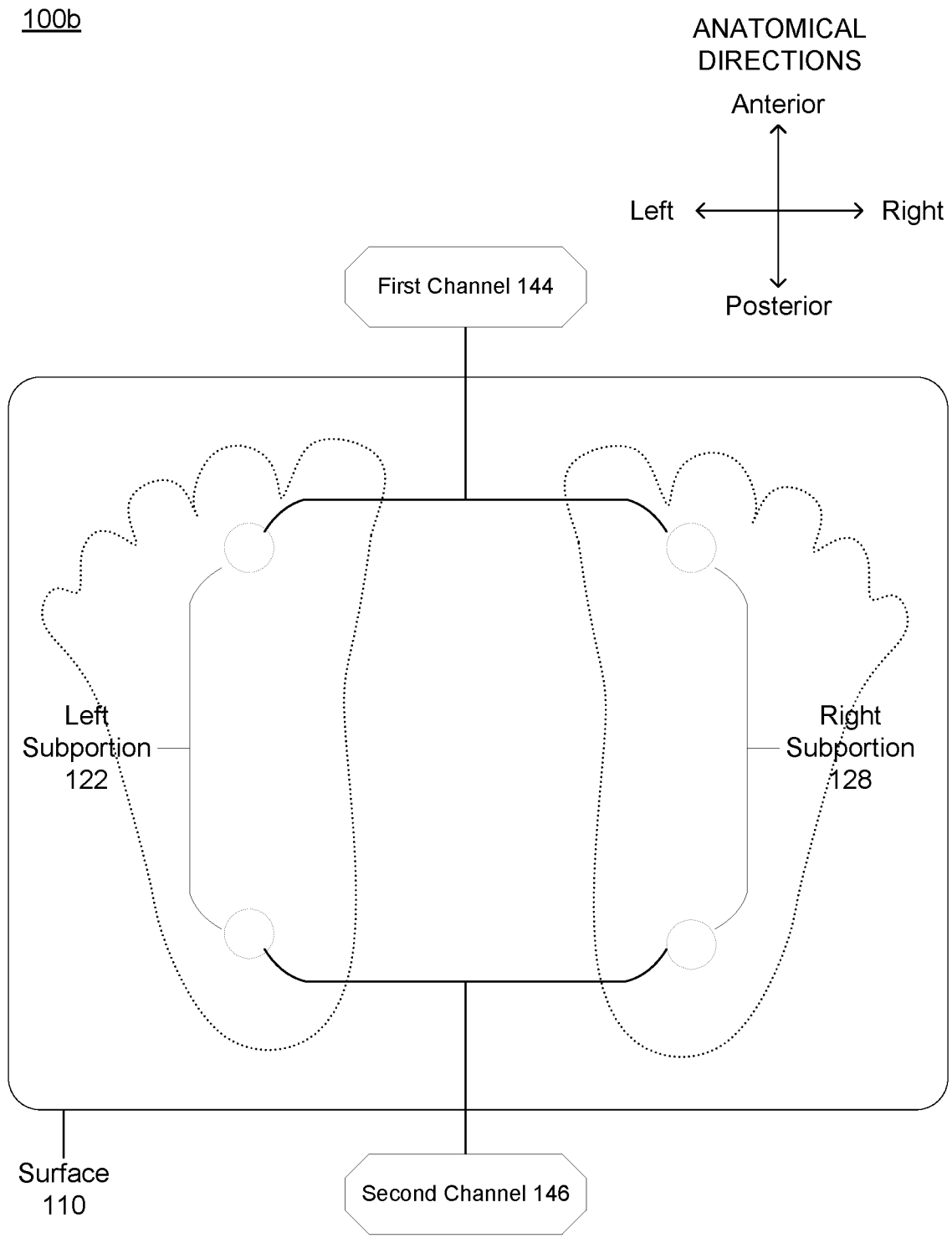
FIG. 1B depicts a plan view of components of the system shown in FIG. 1A.

1. System for Cardiovascular Signal Acquisition, Fusion, and Noise Mitigation FIG. 1A depicts a schematic of a system 100 for cardiovascular signal acquisition, fusion, and noise mitigation, in accordance with one or more embodiments. FIG. 1B depicts a plan view of components of the system 100 shown in FIG. 1A. The system includes a substrate 110, an array of electrodes 120 coupled to the surface and including a left subportion 122 and a right subportion 128, one or more force sensors 130 in mechanical communication with the substrate 110, and electronics subsystem 140 including channels 144 and 146 for generation of electrical signals from the array of electrodes 120, and for relaying and/or pre-processing signals from the force sensor(s) 130. The electronics subsystem 140 also includes components of a computing subsystem 150 and transmission hardware 149 for data communication with other components of the computing subsystem 150, where the computing subsystem 150 includes architecture for generating de-noised signals and for fusion of electrical and mechanical signal data to extract features relevant to analyzing cardiovascular health. The system 100 thus provides structures, subsystem interfaces, and operation modes for signal acquisition and processing, including operations associated with methods described in more detail in Section 2 below.

The system 100 functions to simultaneously acquire electrical and mechanical signals associated with cardiovascular health, and implement signal processing methods to mitigate noise induced by changes in position of the user during signal acquisition, ambient sources, and other sources. The system 100 also includes architecture for receiving different types of electrical and mechanical signals through interfaces with the feet of a user, comparing signals across different vectors defined by device sensor positions, and extracting health-relevant signal components and noise components based upon the comparison(s). In particular, the system 100 is configured for routine assessment of hemodynamic parameters, including systolic time intervals, other temporal parameters (e.g., diastolic time intervals), and other parameters, with design considerations that promote regular use of the system.

1.1 System—Substrate and Electrodes

As shown in FIGS. 1A and 1B, the system includes a substrate 110 that functions to facilitate electrical signal transmission toward the array of electrodes 120 coupled to the substrate 110, and to mechanically support the user's weight in relation to weight measurements and other force-associated signal generation functionality of sensor described in more detail below. The substrate 110 can additionally function to enable display (e.g., with integrated display elements, with transparent materials, with translucent materials, etc.) of information to the user. The information can include information derived from analyses of signals generated by the system, instructions to the user, user verification information, or other types of information.

In morphology, the substrate 110 includes a broad surface that, during use, provides an interface to the feet of the user for electrical and mechanical signal generation. The broad surface of the substrate 110 is planar, but can alternatively include recessed and/or protruding regions defined at the broad surface. Recessed and/or protruding regions of the broad surface can be configured to guide placement of the feet of the user and can include features that are complimentary to the soles of the user's feet.

The substrate 110 has a rectangular footprint when the broad surface is projected onto a horizontal plane, where the rectangular footprint has rounded edges. The substrate 110 can alternatively have any other suitable footprint. In dimensions, the substrate 110 can have a width from 10-50 centimeters, a length from 10-50 centimeters, and a thickness from 0.2-2 centimeters; however, the substrate 110 can alternatively have any other suitable dimensions.

In material composition, the substrate 110 includes at least one region that is composed of glass, where the glass can be processed (e.g., tempered, etc.) to have desired properties in terms of mechanical properties, electrical properties, optical properties, or other properties described in more detail below. The substrate 110 can additionally or alternatively be composed of, or include regions that are composed of one or more of: a polymeric material (e.g., plastic), a metallic material, a ceramic material, and a natural material (e.g., wood, fiber, etc.). The substrate 110 can thus be composed of a single material or can be a composite material to provide suitable physical properties.

In relation to mechanical properties, the material(s) of the substrate 110 can have a compressive strength, a shear strength, a tensile strength, a strength in bending, an elastic modulus, a hardness, a derivative of the above mechanical properties and/or other properties that enable structural support of the user and/or other system elements in various operation modes associated with use of the system 110.

In relation to electrical properties, the material(s) of the substrate 110 can have a conductivity, resistivity, a derivative of the above electrical properties and/or other properties that enable electrical signal transmission from the user's body to electrodes of the system 100 described in more detail below. One or more surfaces of the substrate 110 can be processed to have desired electrical properties. For instance, the broad surface configured to interface with feet of the user can be surface treated with a conductive material (e.g., indium tin oxide) with a desired pattern in relation to signal transduction through the system and/or the body of the user. The bulk material(s) of the substrate 110 can alternatively be selected to have desired electrical properties. As such, the substrate 110 can be an electrically conductive substrate. Additionally or alternatively, one or more portions of the substrate and/or elements coupled to the substrate can be capacitively coupled to the electrodes described below, for instance, through an insulating layer, where in these embodiments, the electrode(s) include a combination of a conductive material covered by an insulating material (and the user's feet are capacitively coupled to the conductive material through the insulating layer). As such, the substrate can include electrically conductive regions, but portions of the system contacting a user are insulating. In relation to optical properties, the material(s) of the substrate 110 can have a transparency or translucency suitable of conveying information to the user by way of an electronic display coupled to, positioned next to, or otherwise optically integrated with the substrate 110 in another manner. The material(s) of the substrate can also be fabricated to manipulate (e.g., reflect, scatter, guide, shape, etc.) light.

As shown in FIGS. 1A and 1B, the system 100 also includes an array of electrodes 120 coupled to the surface and including a left subportion 122 and a right subportion 128. One or more electrodes of the left subportion 122 cooperate with one or more electrodes of the right subportion 128 to generate electrical signals from which parameters relevant to cardiovascular health can be generated, as described in more detail below. One or more electrodes of the left subportion 122 can also provide noise signals that the computing subsystem 150 can use to de-noise the electrical signals. Similarly, one or more electrodes of the right subportion 128 can also provide noise signals that the computing subsystem 150 can use to de-noise the electrical signals. Thus, the arrangement of the array of electrodes 120 in space relative to the substrate 110 can allow the system to improve signal-to-noise (SNR) ratio with signal processing methods, where noise is associated with noise from ambient sources (e.g., 60 Hz mains), noise from motion of a user using the system 100, noise from poor or changing foot contact, and/or any other noise source. Noise sources and methods for signal de-noising are further described in Section 2 below.

As shown in FIG. 1A, when the user interacts with the array of electrodes 120 by contacting the substrate 110 with his/her feet, the system 100 forms an electrical circuit through the user's body. The electrical circuit shown in FIG. 1A is defined through an inferior portion of the user's body, and passes through a left foot region, through a left leg region, across the sagittal plane of the user, through a right leg region, and through a right foot region.

The electrodes of the array of electrodes 120 can be composed of a conductive material (e.g., conductive polymer, metal, etc.).

The array of electrodes 120 generate electrocardiogram (ECG) signals during use. The array of electrodes 120 can additionally generate impedance plethysmography (IPG) signals during use. The array of electrodes 120 can additionally generate other bioelectrical signals upon interacting with the user's body during use of the system 100.

The electrodes are arranged in a 2D array. The 2D array can be a rectangular array, where the rectangular array can have equal numbers of electrodes along its width and height. The size of the array of electrodes 120, in terms of number of electrodes, distribution of electrodes in space, and spacing between electrodes, can be configured based on morphological constraints governed by the substrate 120, other system aspects, or other design considerations. In alternative embodiments, however, the electrodes of the array of electrodes 120 can be arranged in a polygonal array, ellipsoidal array, or in any other suitable manner (e.g., an amorphous array). The electrodes of the array of electrodes 120 can be arranged at central regions of the broad surface of the substrate 110 and/or at peripheral regions of the broad surface of the substrate 110.

The left subportion 122 is electrically isolated from the right subportion 128 to avoid bridging of electrodes of the left subportion 122 with electrodes of the right subportion 128. Electrical isolation can be provided by patterning of electrically conductive regions at the broad surface of the substrate 110, use of insulating materials coupled to the substrate 110, or in another manner.

Figure 2:
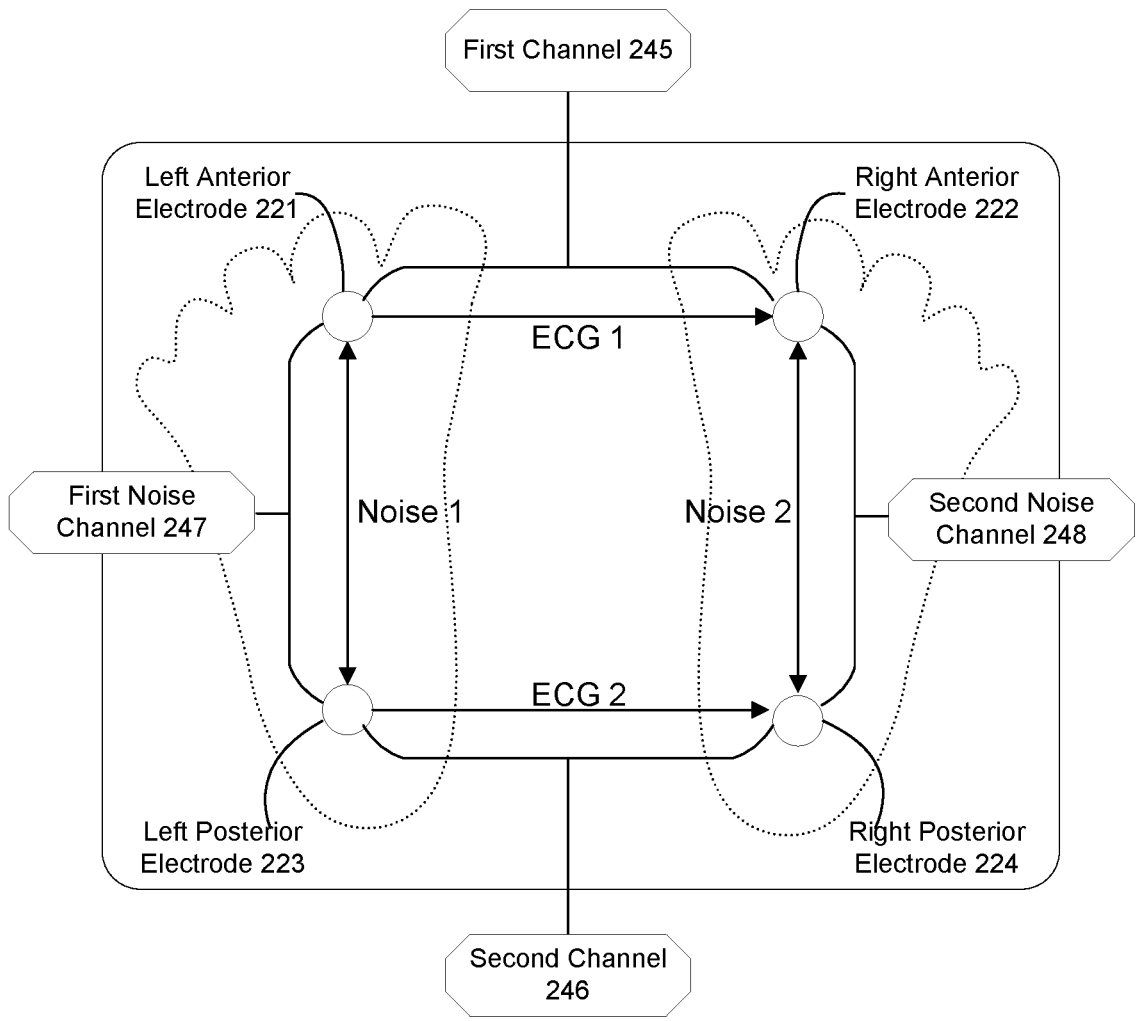
FIG. 2 depicts a plan view of components and vectors associated with electrical signal acquisition and noise acquisition, in accordance with one or more embodiments.

In the embodiment shown in FIG. 2, the array of electrodes 120 includes a left anterior electrode 221, a right anterior electrode 222, a left posterior electrode 223, and a right posterior electrode 224. The left anterior electrode 221 and the left posterior electrode 223 are embodiments of the left subportion 122 of the array of electrodes 120, and the right anterior electrode 222 and the right posterior electrode 224 are embodiments of the right subportion 128 of the array of electrodes 120 described in relation to FIGS. 1A and 1B above. The left anterior electrode 221 and the right anterior electrode 222 are associated with a first electrical signal channel 245 of the electronics subsystem described below, and the left posterior electrode 223 and the right posterior electrode 224 are associated with a second electrical signal channel 246 of the electronics subsystem described below, where each of the first and the second electrical signal channels is associated with a circuit across an inferior sagittal plane of the user's body during use of the system. The left anterior electrode 221 and the left posterior electrode 223 can be used to generate a first noise signal associated with a first noise channel 247, and the right anterior electrode 222 and the right posterior electrode 224 can be used to generate a second noise signal associated with a second noise channel 248, where methods of de-noising are described in more detail in Section 2 below.

Figure 3A:
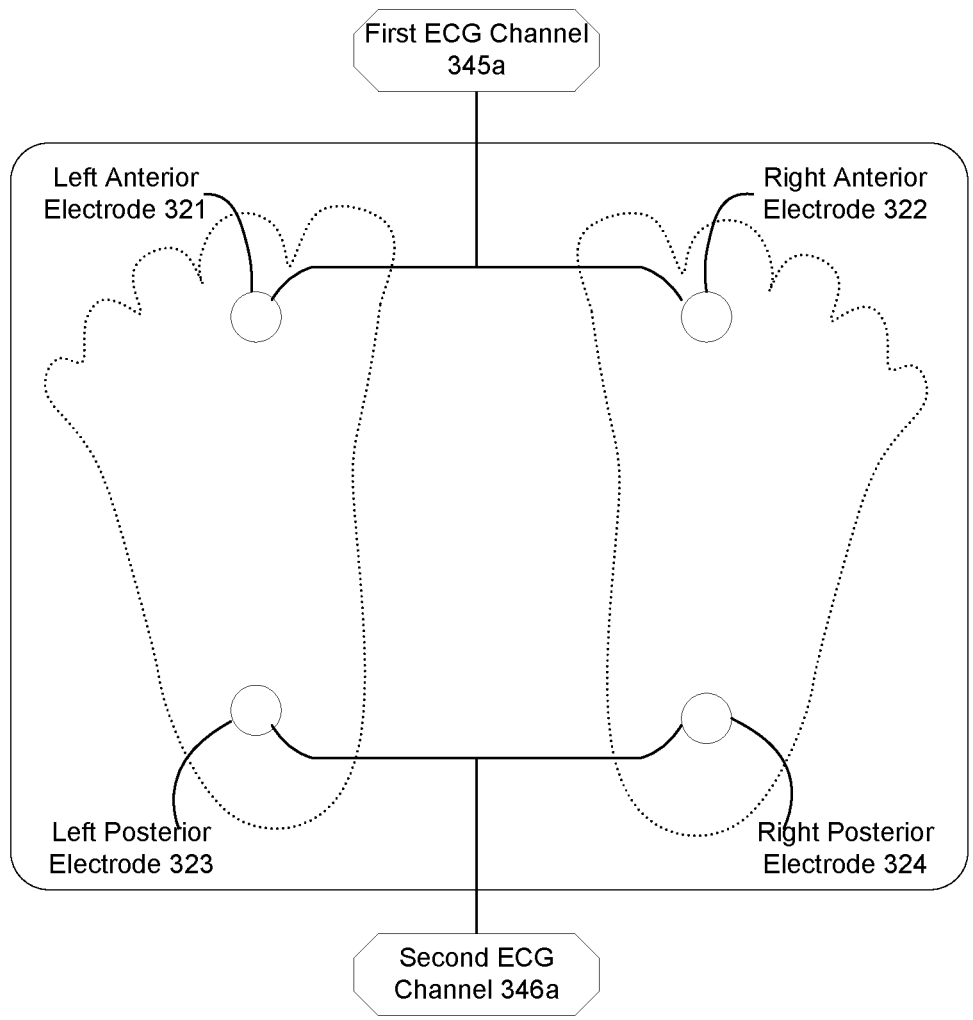
FIG. 3A depicts system component configuration of a first embodiment of the system shown in FIG. 2.

FIG. 3A depicts system component configuration of a first embodiment of the system shown in FIG. 2, where the first embodiment of the system is configured as a 2-channel system for generation of two channels of ECG signals. The first embodiment includes a left anterior electrode 321, a right anterior electrode 322, a left posterior electrode 323, and a right posterior electrode 324, where the left and the right anterior electrodes 321, 322 are associated with a first ECG channel 345$a$ and the left and the right posterior electrodes 323, 324 are associated with a second ECG channel 346$a$. Methods of signal and noise extraction in the 2-channel configuration are described in more detail in Section 2 below.

Figure 3B:
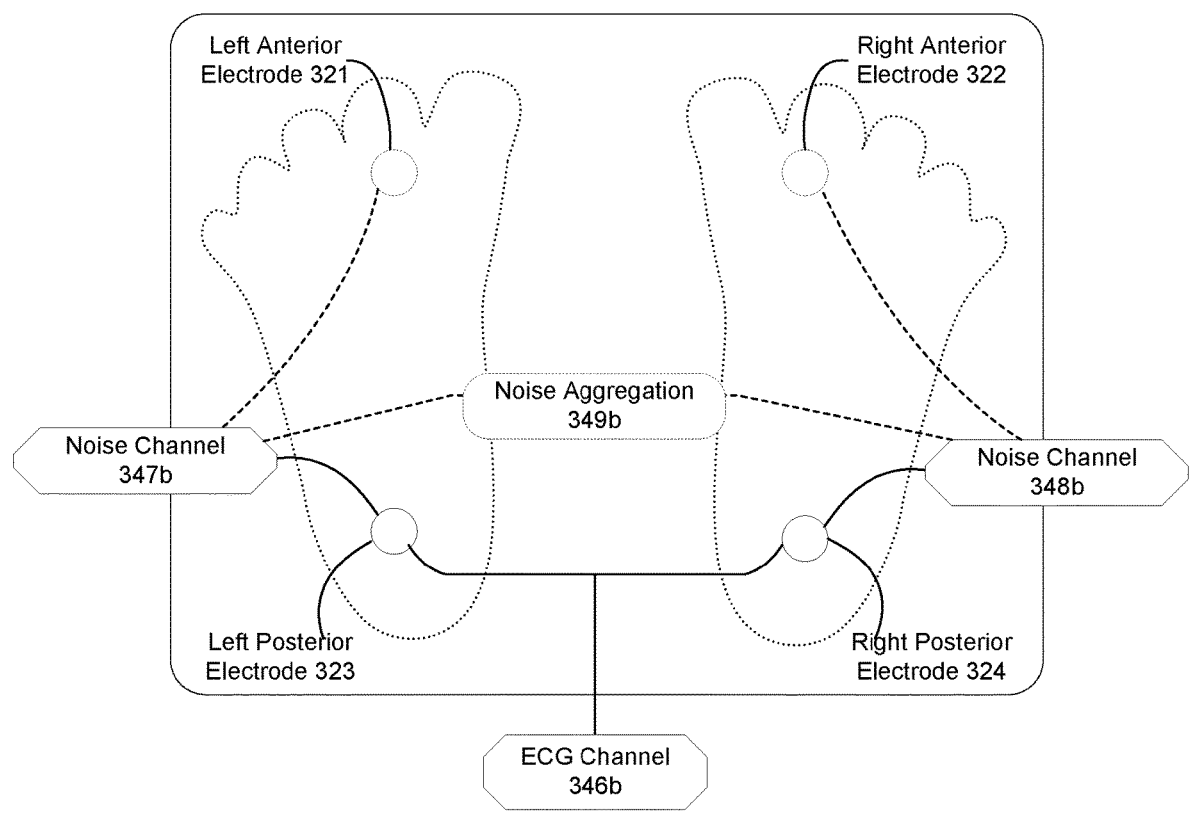
FIG. 3B depicts a system component configuration of a second embodiment of the system shown in FIG. 2.

FIG. 3B depicts a system component configuration of a second embodiment of the system shown in FIG. 2, where the second embodiment of the system is configured as a 3-channel system for generation of channel of ECG signals and two channels of noise signals. The first embodiment includes a left posterior electrode 323 and a right posterior electrode 324, where the left and the right posterior electrodes 323, 324 are associated with an ECG channel 346$b$, the left posterior electrode 323 is associated with a first noise channel 347$b$, and the right posterior electrode 324 is associated with a second noise channel 348$b$. The first and the second noise channels 347$b$, 348$b$ can be coupled to a summation circuit 349$b$ for noise signal aggregation and processing. Methods of signal and noise extraction in the 3-channel configuration are described in more detail in Section 2 below.

Figure 3C:
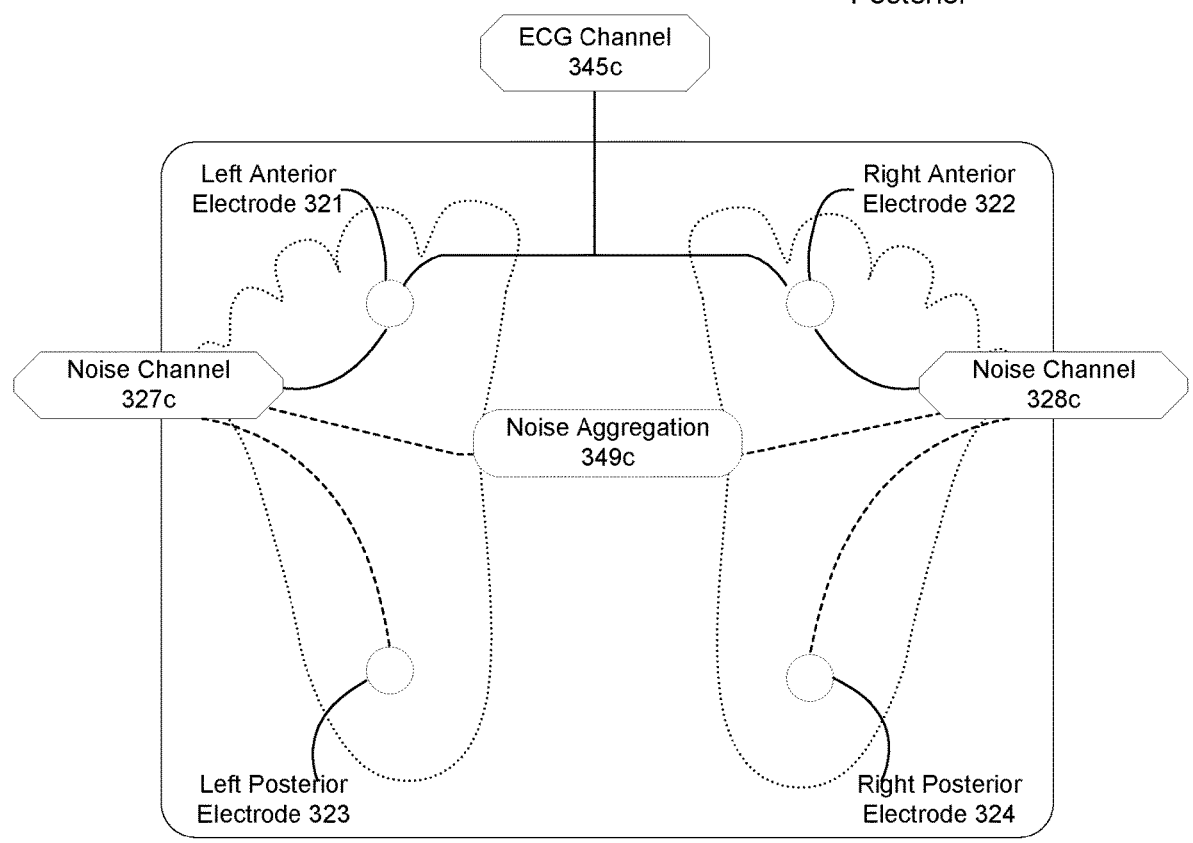
FIG. 3C depicts a system component configuration of a third embodiment of the system shown in FIG. 2.

FIG. 3C depicts a system component configuration of a third embodiment of the system shown in FIG. 2, where the third embodiment of the system is configured as a 3-channel system for generation of channel of ECG signals and two channels of noise signals. The first embodiment includes a left anterior electrode 321 and a right anterior electrode 322, where the left and the right anterior electrodes 321, 322 are associated with an ECG channel 345$c$, the left anterior electrode 321 is associated with a first noise channel 347$c$, and the right anterior electrode 322 is associated with a second noise channel 348$c$. The first and the second noise channels 347$c$, 348$c$ can be coupled to a summation circuit 349$c$. Methods of signal and noise extraction in the 3-channel configuration are described in more detail in Section 2 below.

Figure 3D:
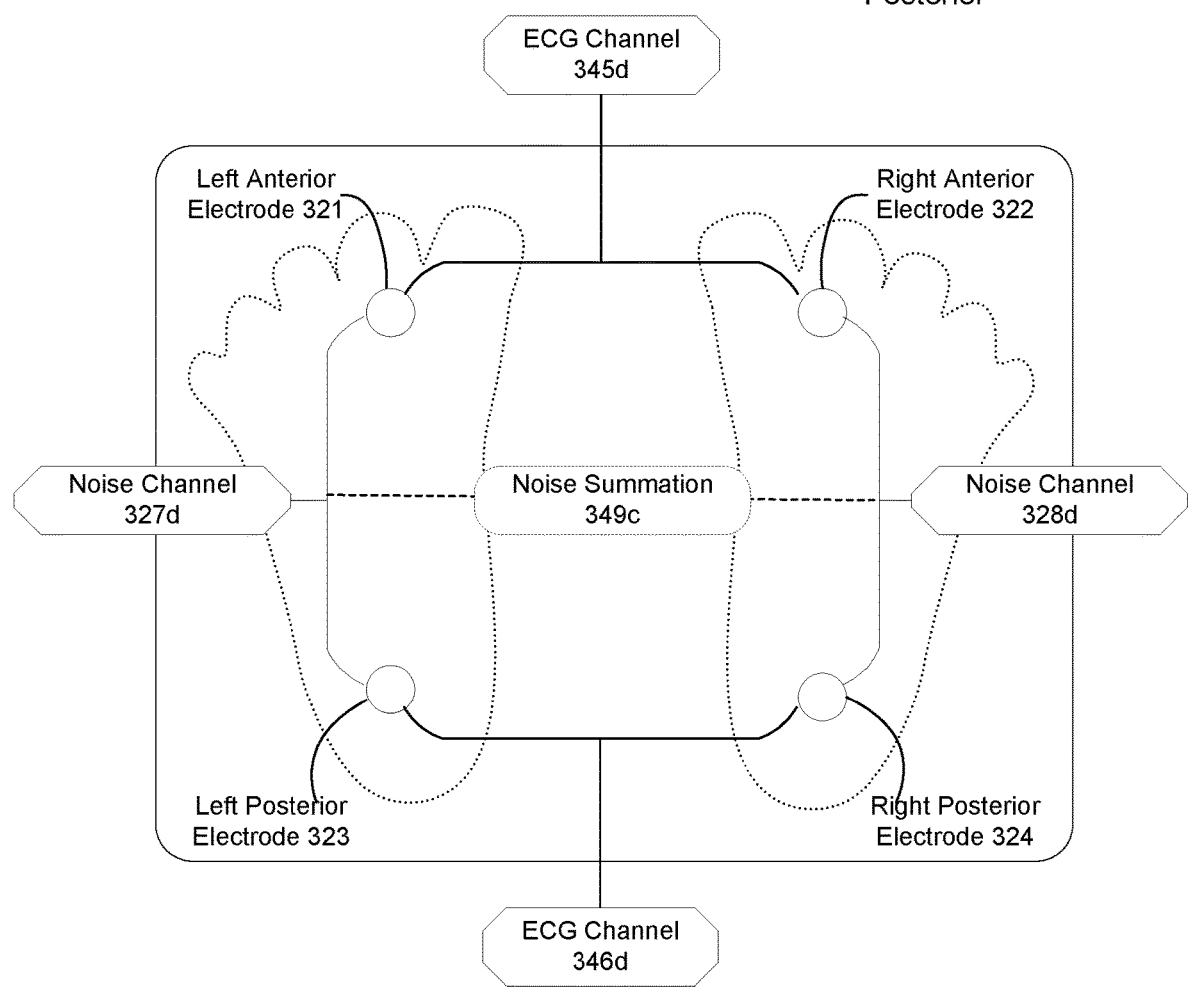
FIG. 3D depicts a system component configuration of a fourth embodiment of the system shown in FIG. 2.

FIG. 3D depicts a system component configuration of a fourth embodiment of the system shown in FIG. 2, where the fourth embodiment of the system is configured as a 4-channel system for generation of two channels of ECG signals and two channels of noise signals. The first embodiment includes a left anterior electrode 321, a right anterior electrode 322, a left posterior electrode 323 and a right posterior electrode 324, where the left and the right anterior electrodes 321, 322 are associated with a first ECG channel 345d, the left and the right posterior electrodes 323, 324 are associated with a second ECG channel 346d, the left anterior and posterior electrodes 321, 323 are associated with a first noise channel 347d, and the right anterior and posterior electrodes 322, 324 are associated with a second noise channel 348d. The first and the second noise channels 347d, 348d can be coupled to a summation circuit 349d. Methods of signal and noise extraction in the 4-channel configuration are described in more detail in Section 2 below.

Figure 4:
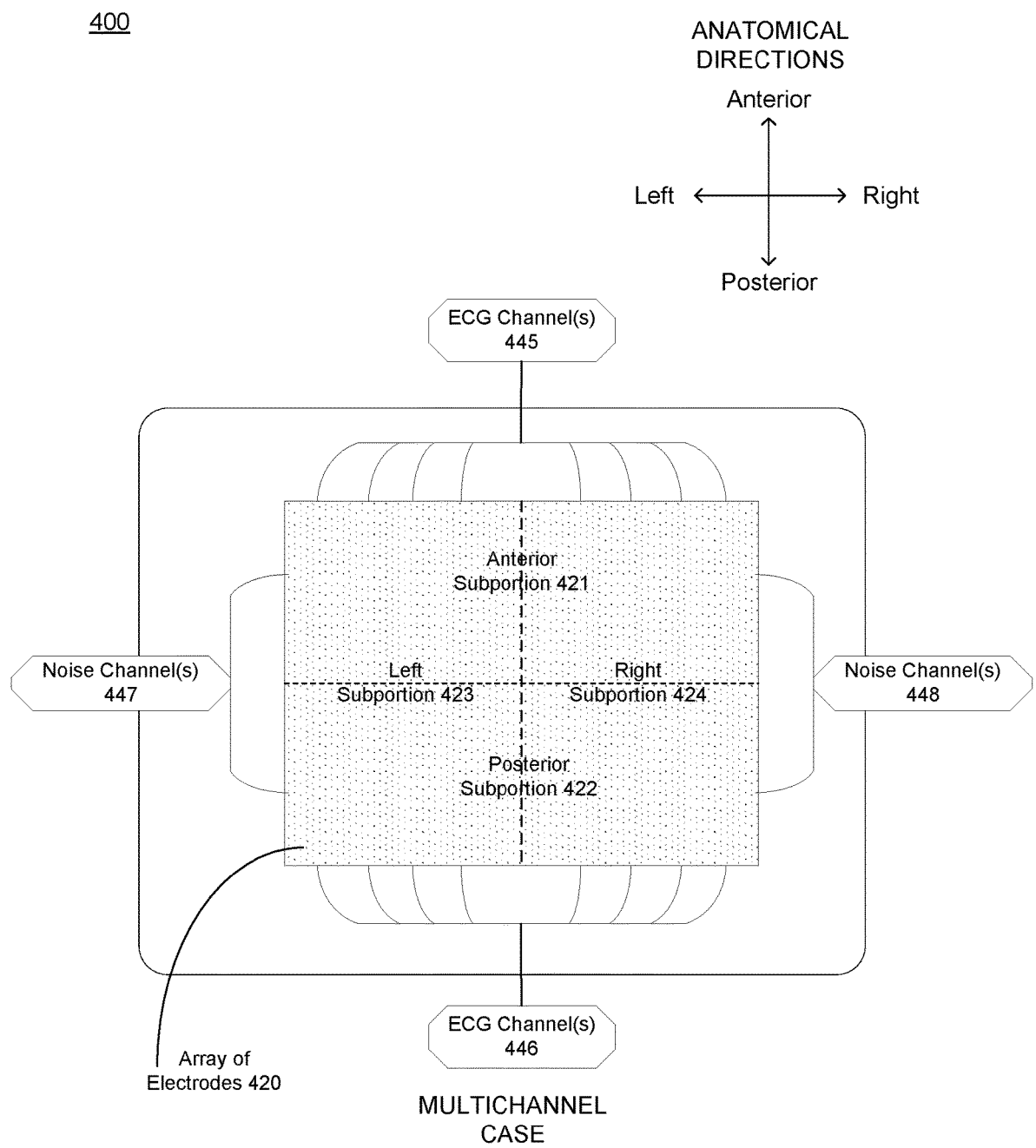
FIG. 4 depicts a plan view of a system component configuration, in accordance with one or more embodiments.

In a variation related to FIGS. 3A-3D, the system is configured as a 3-channel (or 4-channel) system for generation of different channels of noise and one channel (or two channels) of ECG signals. In more detail, the system includes a left anterior electrode 321, a right anterior electrode 322, a left posterior electrode 323 and a right posterior electrode 324, where both the left anterior and posterior electrodes 321, 323 are used to derive a noise source, and/or both the right anterior and posterior electrodes 322, 324 are used to derive a noise source. The left and the right posterior electrodes 323, 324 are associated with a first ECG channel and/or the left and right anterior electrodes 321, 322 are associated with a second ECG channel. FIG. 4 depicts a plan view of a system component configuration, in accordance with one or more embodiments. The embodiment shown in FIG. 4 is configured as a multichannel system for generation of multiple channels of ECG signals and/or multiple channels of noise signals. The array of electrodes 420 is arranged as an anterior subportion 421, a posterior subportion 422, a left subportion 423, and a right subportion 424, where groupings of the anterior subportion 421 are associated with one or more ECG channels 445, groupings of the posterior subportion 422 are associated with one or more ECG channels 446, groupings of the left subportion 423 are associated with one or more noise channels 447, and groupings of the right subportion 424 are associated with one or more noise channels 448.

1.2 System—Other Sensors

As shown in FIGS. 1A and 1B, embodiments of the system also include one or more force sensors 130 in mechanical communication with the surface 110, where the force sensors can generate signals that are indicative of weight of the user (e.g., as the user steps onto the substrate 110) and/or can detect forces and changes in forces that are indicative of other physiologically-relevant parameters. The force sensors 130, for instance, can generate ballistocardiogram (BCG) signals from forces generated by cardiovascular physiological behavior, which are detected and fused with other signal data according to methods described below.

Embodiments of the system can additionally or alternatively include one or more electrodes coupled to a right leg drive (RLD) electrode, where such a configuration generates a signal that is derived, at least in part, from a common mode portion of at least one of the ECG signals applied back to the body of the user, during use. Such a configuration operates to enable removal of common mode interference and can bias the ECG signals to within an input voltage range of respective signal amplifiers. The RLD signal can be derived from a single ECG signal or a combination of multiple ECG signals. In a configuration without an RLD electrode and associated circuitry, a signal input is AC-coupled and biased at mid-supply voltage to bias the ECG signals to within an input voltage range of respective signal amplifiers.

Embodiments of the system can additionally or alternatively include other sensors and/or biometric sensors for sensing aspects of the user, the user's physiology, and/or the environment of the user. Other sensors can include audio sensors (e.g., microphones), motion/orientation sensors (e.g., accelerometers, gyroscopes, inertial measurement units, etc.), respiration sensors (e.g., plethysmography sensors), cardiovascular sensors (e.g., electrical signal-based cardiovascular sensors, radar-based cardiovascular sensors, force-based cardiovascular sensors, etc.), temperature sensors for monitoring environmental temperature (e.g., ambient temperature) and/or body temperature of the user, moistures sensors (e.g., for detecting environmental moisture), optical sensors (e.g., for optically detecting blood flow through user body tissue, optical sensors for detecting contact with the user), capacitive touch sensors, other electrophysiology sensors (e.g., skin conductance sensors), and/or any other suitable sensors.

1.3 System—Electronics and Computing Subsystem

As shown in FIGS. 1A and 1B, embodiments of the system also include an electronics subsystem 140 including channels 144 and 146 for generation of electrical signals from the array of electrodes 120, and for relaying and/or pre-processing signals from the force sensor(s) 130, where channel configurations are described in more detail above in relation to configurations of the array of electrodes in different embodiments.

The electronics subsystem 140 includes components for receiving, conditioning, and relaying signals generated by the array of electrodes 120 and/or the force sensor(s) 130. For instance, electrical signals detected by the system from the feet of a user are on the order of 10-100 times smaller than the electrical signals collected by traditional methods (e.g., through the chest, hands, or upper extremity limbs), which significantly decreases signal-to-noise ratio. Therefore, the electronics subsystem 140 can include conditioning components, such as a high-resolution A/D converter and/or one or more filters. The electronics subsystem 140 can also include components that provide power and/or manages power provision to one or more other system components. For instance, the electronics subsystem 140 can include a battery (e.g., rechargeable battery, non-rechargeable battery) electrically coupled to a power management system that maintains desired circuit voltages and/or current draw appropriate for different system components. Power-associated components of the electronics subsystem 140 can be retained within a housing of the system, where the electronics subsystem 140 can be electrically and/or physically coupled to one or more of the substrate 110, the array of electrodes 120, and the force sensor(s) through the housing.

The electronics subsystem 140 also includes components of a computing subsystem 150 and can also include data transmission hardware 149 for data communication with other components of the computing subsystem 150 that are remote from device components that the user physically interacts with. Remote computing components can be implemented at other networked computers, remote servers, in the cloud, and/or in another computing platform. The transmission hardware 149 can include receive and/or transmit components for handling data transfer between electronics of the device that the user physically interacts with and remote computing components through a network. Furthermore, the transmission hardware 149 can provide a wired and/or wireless (e.g., WiFi, Bluetooth LE, etc.) interface with the network or other remote computing subsystem components.

In relation to methods described in Section 2 below, the computing subsystem 150 can also include a non-transitory computer-readable storage medium containing computer program code for implementing one or more portions of the method(s) described below. For instance, the computing subsystem 150 can include program code and architecture for generating an electrocardiogram (ECG) signal from a left subportion 122 and a right subportion 128 of the array of electrodes 120, generating a first noise signal from the left subportion 122 and/or a second noise signal from the right subportion 128 of the array of electrodes, and generating a de-noised ECG signal upon processing the ECG signal with the first and/or the second noise signals.

The computing subsystem 150 can also include architecture for storing instructions in non-transitory computer readable media for controlling operation states of electrodes and/or sensors, monitoring states of components coupled to the computing subsystem 150, storing data in memory, coordinating data transfer (e.g., in relation to the transmission hardware 149), and/or performing any other suitable computing function of the system. The computing component 160a can additionally or alternatively include signal conditioning elements (e.g., amplifiers, filters, analog-to-digital converters, digital-to-analog converters, etc.) for processing signal outputs of electrodes and sensors of the system 100.

2. Method—Extracting and De-Noising Electrical Signals

Figure 5A:
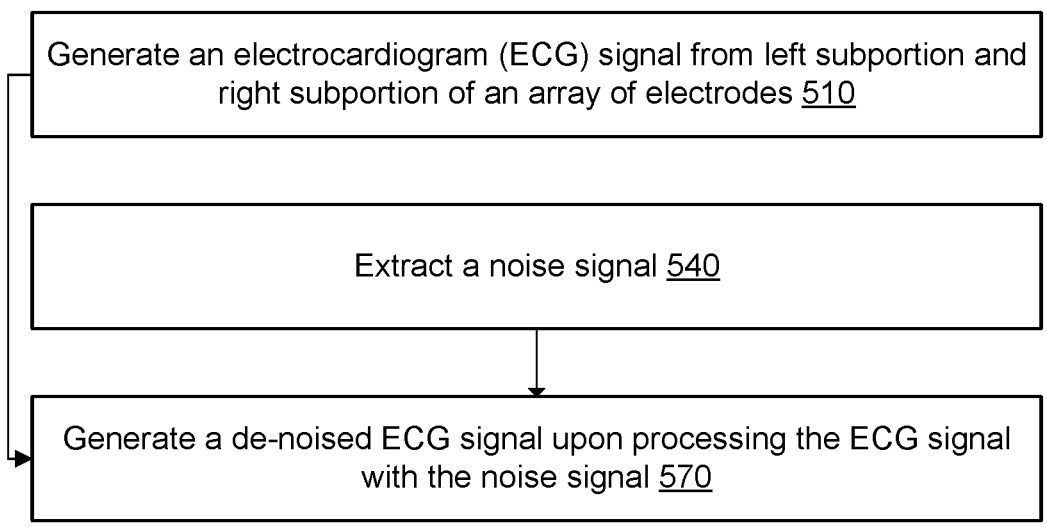
FIG. 5A depicts a flowchart of a method for cardiovascular signal acquisition and noise mitigation, in accordance with one or more embodiments.

FIG. 5A depicts a flowchart of a method 500 for cardiovascular signal acquisition and noise mitigation, in accordance with one or more embodiments. As shown in FIG. 5A, the array of electrodes generates one or more ECG signals from the left and the right subportions of the array 510. Then, the computing subsystem (e.g., components of the electronics subsystem and/or the computing subsystem described above) extracts one or more noise signals 540 and generates one or more de-noised ECG signals 570 upon processing the one or more ECG signals to isolate components of the noise signal(s) from the ECG signals.

The method 500 functions to acquire electrical signals associated with cardiovascular health in a non-standard manner and with a system designed to promote routine usage by a user, and also functions to implement sensor distributions in space to mitigate noise induced by ambient sources, user motion (e.g., feet motion), and other sources. The method can include receiving electrical signals through the feet of a user, comparing signals across different vectors defined by device sensor positions, and extracting health-relevant signal components and noise components based upon noise-isolation and extraction methods. As such, the method 500 significantly increases signal-to-noise ratios for electrical signals acquired through feet of the user. While applications of the method 500 for de-noising ECG signals are described, the method 500 can additionally or alternatively be used to denoise other electrical signals (e.g., IPG signals, other passive electrical signals, other active electrical signals).

The method 500 can be implemented by one or more portions of the system embodiment(s) described above, where anterior, posterior, left, and right electrode portions of an array of electrodes can provide source signals that are processed to generate de-noised signals of interest. As configured by the structure of embodiments of the system described above, noise and artifacts present in outputs from anterior electrodes is largely uncorrelated with noise and artifacts present in outputs from posterior electrodes. Furthermore, as configured by the structure of embodiments of the system described above, anterior and posterior subportions of electrodes output both signal and noise components, while left and right subportions of electrodes output only noise components because they are not positioned across the body and heart. In more detail, noise outputs from left and right subportions of electrodes produce noise signal components in varying proportions and combinations relative to noise signal components from anterior and posterior subportions of electrodes.

2.1 Method—Noise Contributions

Electrical signals detected by the system from the feet of a user are on the order of 10-100 times smaller than the electrical signals collected by traditional methods (e.g., through the chest, hands, or upper extremity limbs), which significantly decreases signal-to-noise ratio. As such, noise factors can have a much larger effect on signal acquisition and/or processing as compared to traditional methods for signal acquisition in relation to cardiovascular health. In relation to noise contributions to the ECG signals (or other electrical signals) generated using the array of electrodes, noise can come from ambient sources (e.g., 60 Hz mains, 50 Hz mains, thermal fluctuations in the environment, industrial noise, etc.). Noise can also come from motion of the user while interfacing with the array of electrodes. For instance, in relation to the weighing scale form factor of the device described above, motion of the user's body and/or or feet, such as swaying motions while measuring body weight, curling of the feet, shifting of the feet, motions to maintain balance, poor contact between foot regions and the electrode (s), and/or other motions can induce significant noise that impacts the SNR of the desired signal(s). Such motions can induce electromyography (EMG) artifacts in electrical signals due to generation of electrical signals from muscular contraction and/or relaxation behavior. Such motions can additionally or alternatively induce force-associated artifacts that can interfere with force associated measurements of the system.

Methods for isolating and extracting noise induced by these and other sources are described below in relation to FIGS. 5B-5F, where noise can be extracted using blind source separation techniques (e.g., using independent component analysis), using adaptive filtering operations, using sensor channel windowing operations, using nonparametric spectral estimation processes, and/or using other operations that isolate desired signals and undesired noise signal components from source signals that include both desired components and noise.

2.2 Method—Signal De-Noising Using Blind Source Separation Techniques

Figure 5B:
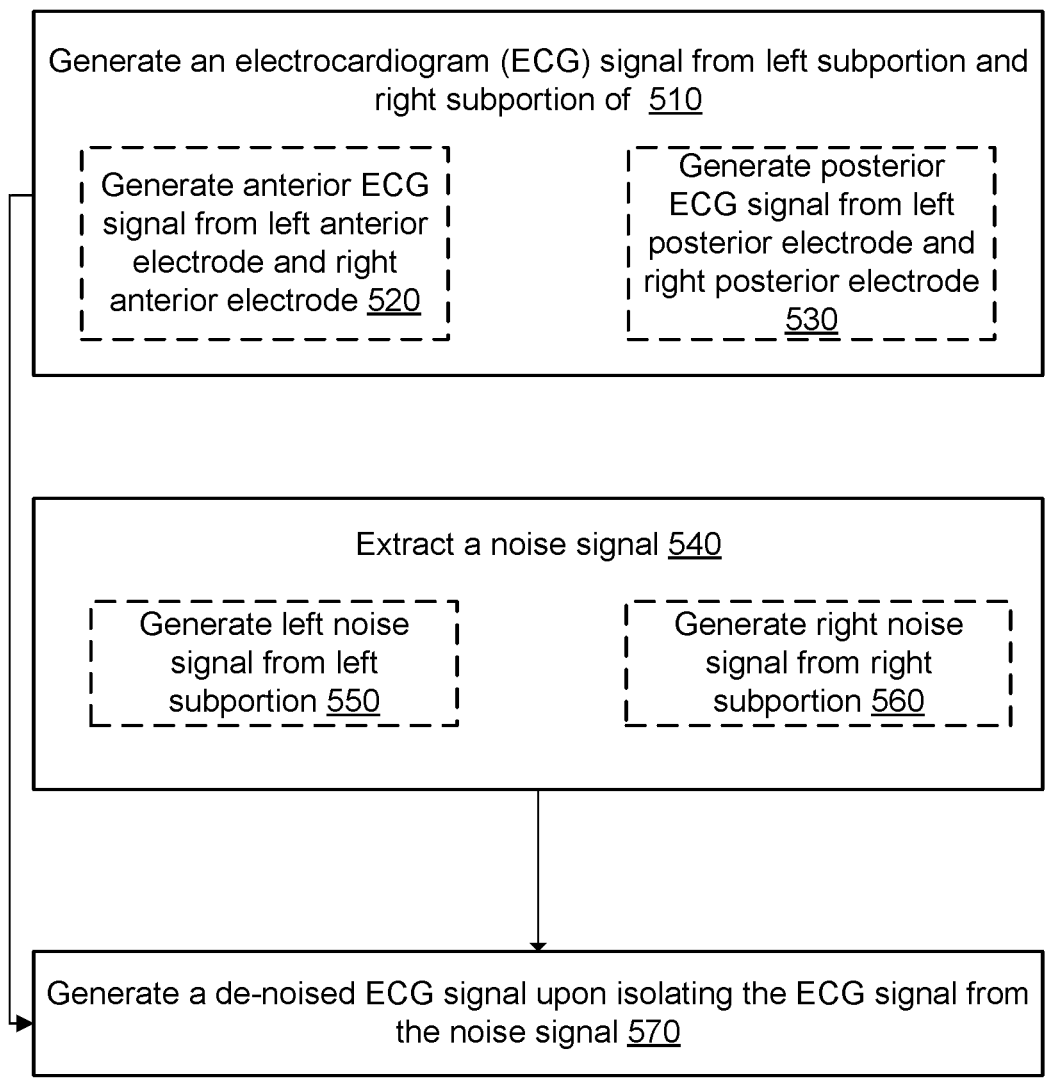
FIG. 5B depicts a flowchart of a first embodiment of the method shown in FIG. 5A.

FIG. 5B depicts a flowchart of a first embodiment of the method shown in FIG. 5A, where independent ECG signal sources can be estimated from source signals that have noise. The method 500b of FIG. 5B can be implemented using a two-channel array configuration (e.g., the configuration shown in FIG. 3A), using a three-channel array configuration (e.g., the configuration shown in FIG. 3B or 3C), using a four-channel array configuration (e.g., the configuration shown in FIG. 3A), or using a configuration with more than four channels. The computing subsystem, in cooperation with the array of electrodes, thus generates 510 one or more ECG signals including an anterior ECG signal 520 and/or a posterior ECG signal 530, and extracts 540 a noise signal including a left noise signal and/or a right noise signal 560, with separation 570 of de-noised components from noise components based on electrode array configuration.

In one embodiment of FIG. 5B, the computing subsystem, in cooperation with electronics components that receive source signals from the array of electrodes, processes input signals from input channels and produces output signals where independent desired signal components are separated from undesired noise components. In this embodiment, the computing system includes architecture in code for performing an independent component analysis (ICA) operation the separates multivariate signals from the input channels into subcomponents associated with desired signals and noise.

As noted above in relation to FIGS. 3A-3D, the input channels can be an anterior ECG channel coupled to left and right anterior electrodes and a posterior ECG channel coupled to left and right posterior electrodes (as in the 2-channel configuration of FIG. 3A), where the output of the ICA operation recreates a new anterior ECG signal and a new posterior ECG signal with noise components separated out. Alternatively, the input channels can be a posterior ECG channel coupled to left and right posterior electrodes and two noise channels coupled to left electrodes and right electrodes, respectively (as in the 3-channel configuration of FIG. 3B), where the output of the ICA operation recreates a new posterior ECG signal and isolated noise signals associated with the two noise channels. Alternatively, the input channels can be an anterior ECG channel coupled to left and right anterior electrodes and two noise channels coupled to left electrodes and right electrodes, respectively (as in the 3-channel configuration of FIG. 3C), where the output of the ICA operation recreates a new anterior ECG signal and isolated noise signals associated with the two noise channels. Alternatively, the input channels can be an anterior ECG channel coupled to left and right anterior electrodes, a posterior ECG channel coupled to left and right posterior electrodes, and two noise channels coupled to left electrodes and right electrodes, respectively (as in the 4-channel configuration of FIG. 3D), where the output of the ICA operation recreates a new anterior ECG signal, a new posterior ECG signal, and isolated noise signals associated with the two noise channels.

The ICA operation implemented by the computing subsystem separates the independent signal and noise components by increasing the statistical independence of the estimated signal and noise components, with a parallel or deflational ICA algorithm. The ICA operation can be based on maximization of non-Gaussianity (e.g., as motivated by central limit theory, considering kurtosis, considering negentropy), or minimization of mutual information (e.g., considering maximum entropy, based on a divergence factor). The ICA operation can be based on a non-linear function or a linear function that transforms the multivariate input into resolved independent components. In alternative embodiments, another blind source separation operation, such as principal components analysis, singular value decomposition, dependent component analysis, matrix factorization, coding and decoding, stationary subspace analysis, or another operation can be used to resolve signal and noise components.

2.3 Method—Signal De-Noising Using Adaptive Filtering Techniques

Figure 5C:
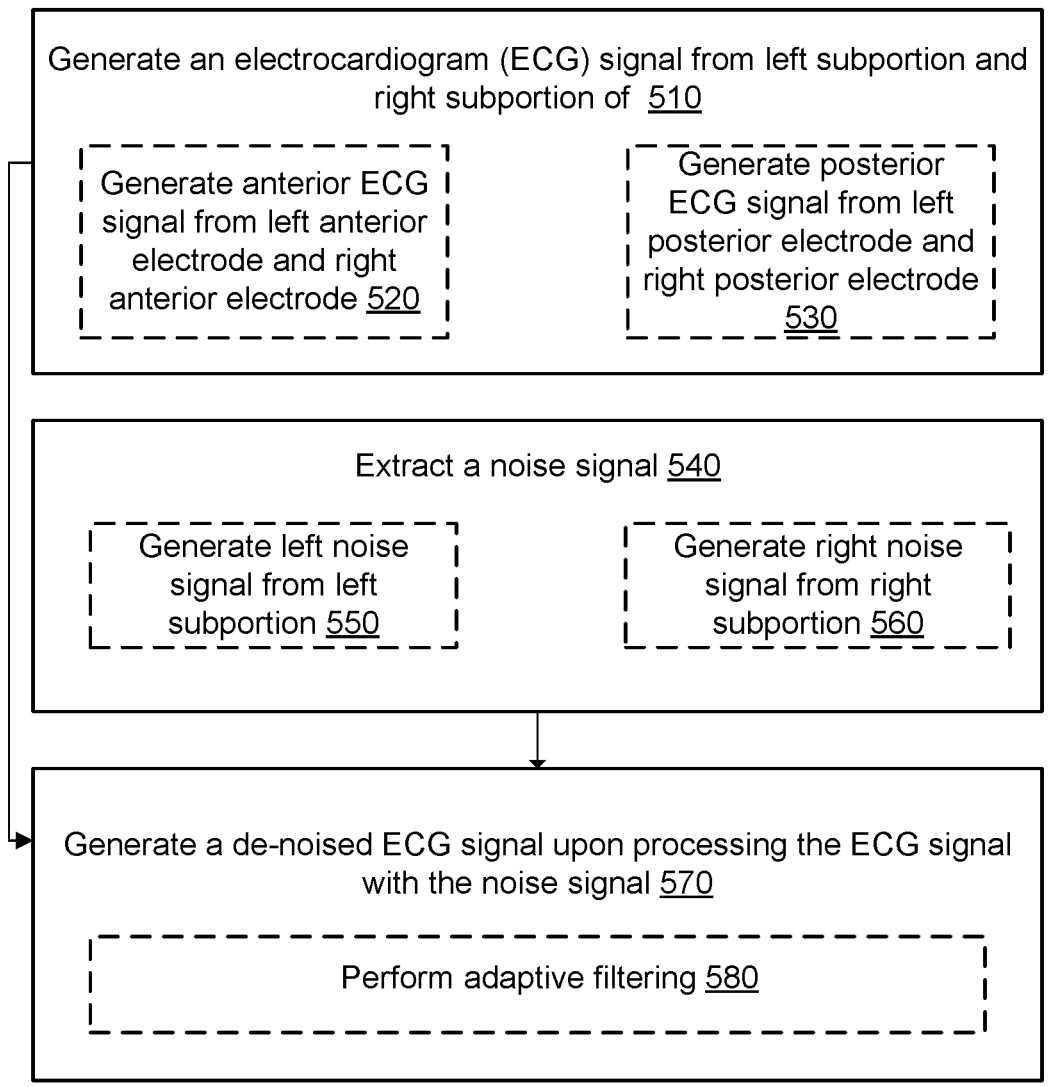
FIG. 5C depicts a flowchart of a second embodiment of the method shown in FIG. 5A.

FIG. 5C depicts a flowchart of a second embodiment of the method shown in FIG. 5A, where the second embodiment implements an adaptive filtering operation. The method 500c of FIG. 5C can be implemented using a four-channel array configuration (e.g., the configuration shown in FIG. 3D) or with another array/channel configuration. In performing the method 500c, the computing subsystem, in cooperation with the array of electrodes, generates 510 one or more ECG signals including an anterior ECG signal 520 and a posterior ECG signal 530, and extracts 540 a noise signal including a left noise signal and/or a right noise signal 560, with separation 570 of de-noised components from noise components based on an adaptive filtering operation.

The adaptive filtering operation can use an affine projection algorithm with the filter equation $y(k)=XT(k)*w(k)$, where y is the filtered signal, X is the filter input matrix that is a function of x, where x is a vector of adaptive filter parameters, w is a function for adaptation of adaptive parameters, and k is a time index. The input signals to the affine projection operation are the anterior and posterior ECG signals and the summation of signals from two noise channels.

The adaptive filtering operation can alternatively use a recursive least squares algorithm or a least mean squares algorithm with the filter equation $y(k)=xT(k)*w(k)$, where y is the filtered signal, x is a vector of adaptive filter parameters, w is a function for adaptation of adaptive parameters, and k is a time index. The input signals to the least squares operation(s) are the anterior and posterior ECG signals and the summation of signals from two noise channels.

Alternative embodiments of the adaptive filtering operation can use a generalized normalized gradient descent algorithm, a least mean fourth algorithm, or another suitable adaptive filtering algorithm.

2.4 Method—Signal De-Noising Using Sensor Selection Techniques

Figure 5D:
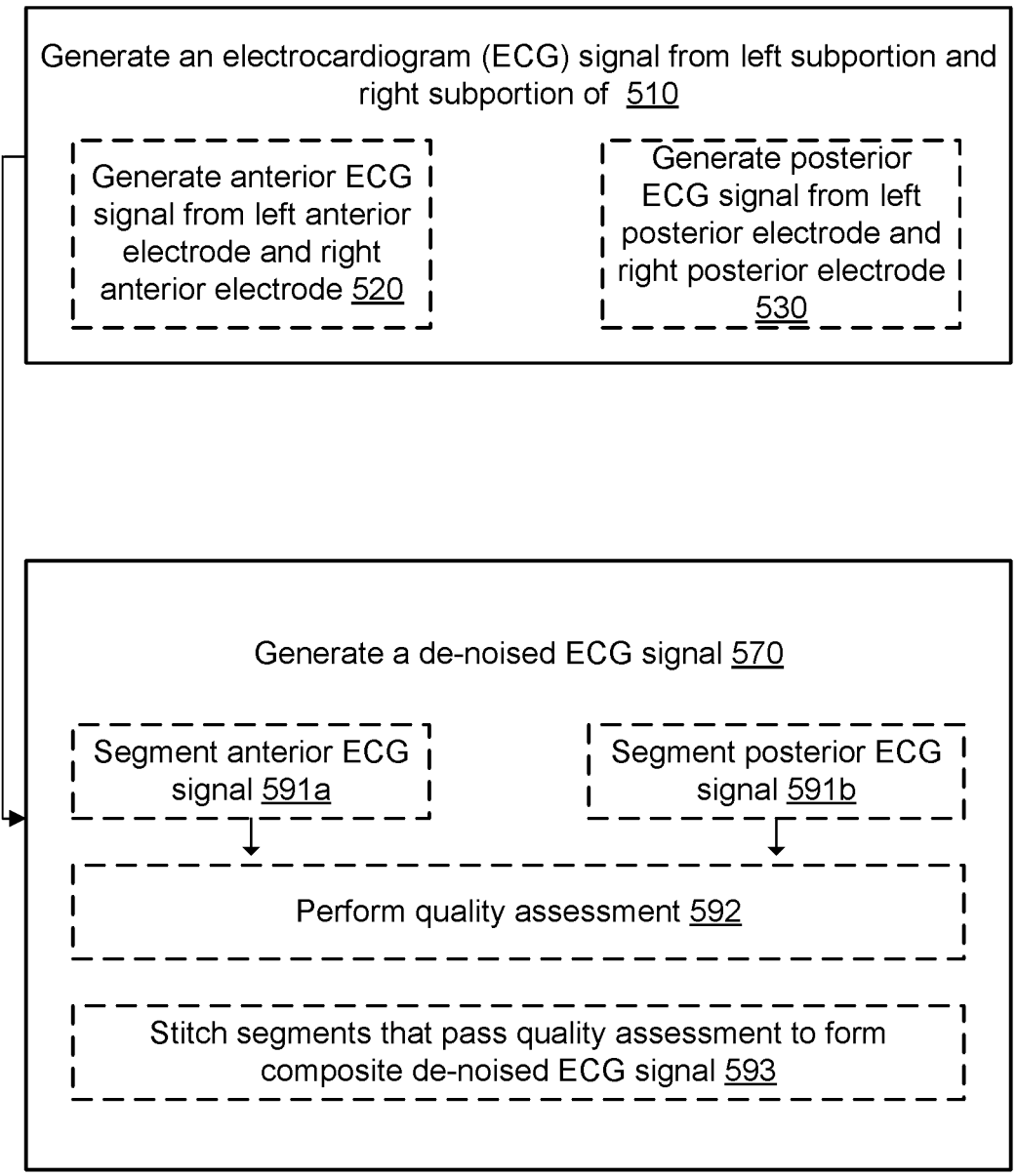
FIG. 5D depicts a flowchart of a third embodiment of the method shown in FIG. 5A.
Figure 5E:
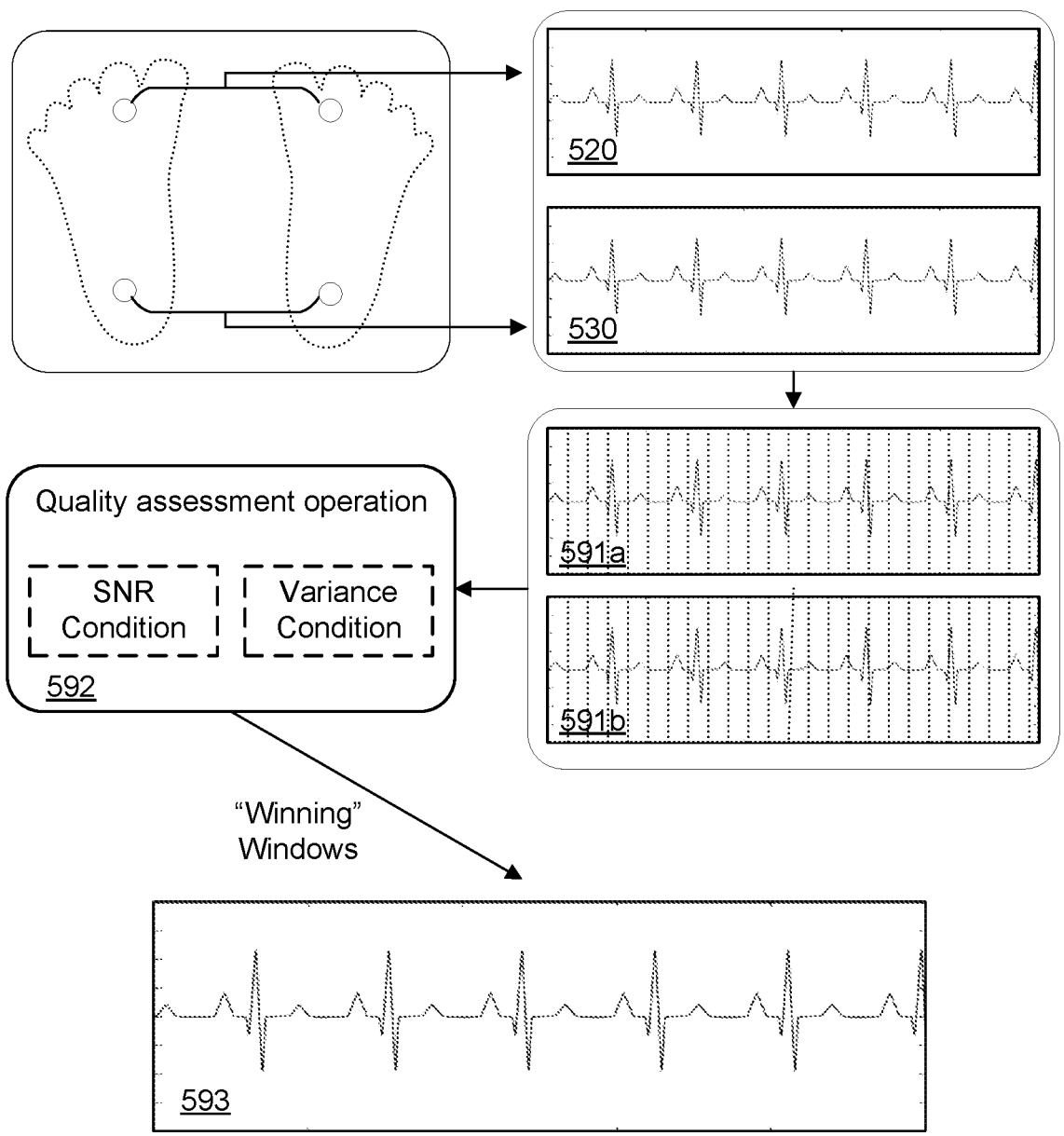
FIG. 5E depicts a schematic flow of the embodiment of the method shown in FIG. 5D.

FIG. 5D depicts a flowchart of a third embodiment of the method shown in FIG. 5A, and FIG. 5E depicts a schematic flow of the embodiment of the method shown in FIG. 5D. In performing the method 500d, the computing subsystem, in cooperation with the array of electrodes, generates 510 one or more ECG signals including an anterior ECG signal 520 and a posterior ECG signal 530, and generates 570 a de-noised signal upon segmenting the anterior ECG signal 591a and the posterior ECG signal 591b, performs a quality assessment operation 592 based on analysis of noise present in each segment of the anterior ECG signal and the posterior ECG signal, and stitches segments that pass the quality assessment operation 593 to form a composite de-noised ECG signal. In relation to segmentation, the computing subsystem can segment signals into windows with a desired window length (e.g., 1 second, less than one second, more than 1 second), where the windows can be non-overlapping or overlapping. In the quality assessment operation, the criteria for selection of the signal window to include in the composite de-noised ECG signal can be based on a SNR criterion or a variance-associated criterion. In more detail, for each matching window across the anterior ECG signal and the posterior ECG signal, the computing subsystem can determine which window has less noise based on the SNR or the variance-associated criterion, and pass the "winning" window onward for stitching to generate the composite de-noised ECG signal.

2.5 Method—Signal De-Noising Using Nonparametric Spectral Estimation Techniques

Figure 5F:
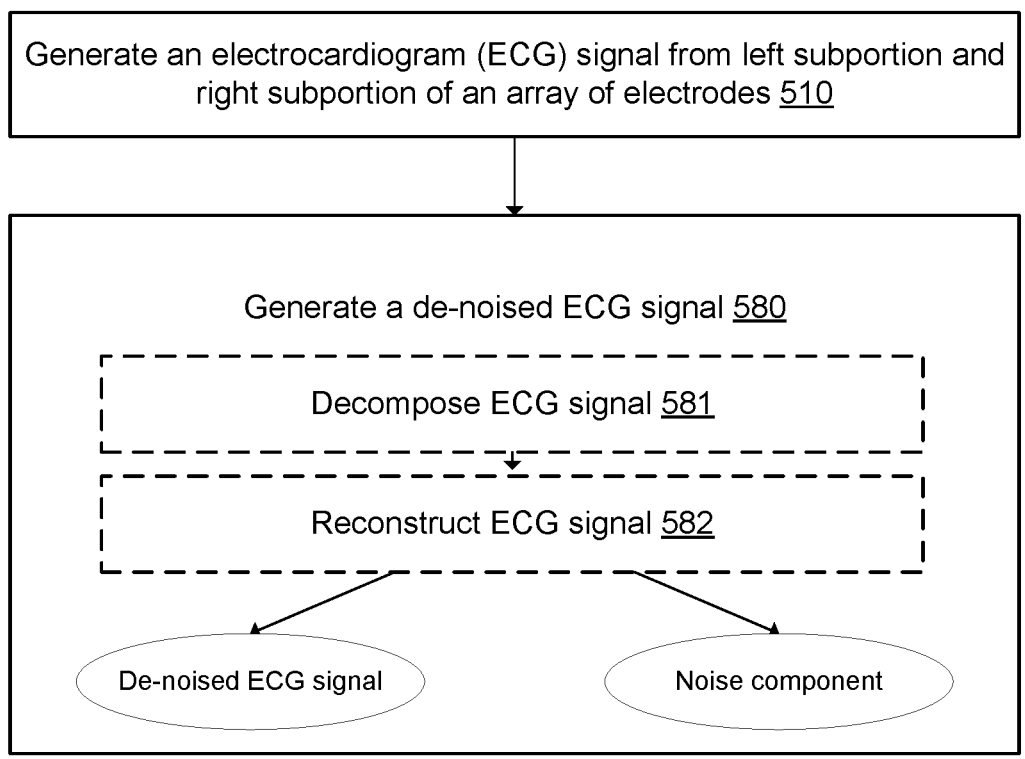
FIG. 5F depicts a flowchart of a variation of the method for cardiovascular signal acquisition and noise mitigation shown in FIG. 5A.

FIG. 5F depicts a flowchart of a variation of the method for cardiovascular signal acquisition and noise mitigation shown in FIG. 5A. In performing the method 500f, the computing subsystem, in cooperation with the array of electrodes, performs a non-parametric spectral estimation process by generating 510 one or more ECG signals from left and right subportions of an array of electrodes, and generating 580 a de-noised signal upon decomposing the ECG signal(s) 581 and reconstructing the ECG signal(s) 582 to extract a de-noised signal component and a noise component. In performing the method 500*f*, the computing subsystem can extract the de-noised ECG signals by using the quasi-periodic nature of the ECG signal(s). In a specific example of 500*f*, the computing subsystem embeds an input ECG signal (e.g., an anterior ECG signal, a posterior ECG signal) into a Hankel matrix having a desired length (e.g., of 100 samples, of less than 100 samples, of more than 100 samples) based on accuracy considerations, where longer matrices produce greater accuracy, but are computationally expensive. The computing subsystem then uses a singular value decomposition operation with the Hankel matrix to decompose the input signal. Then, the computing subsystem reconstructs the ECG signal by splitting the output from the decomposition operation into two groups including a first group for the ECG signal component and a second group for the noise signal component. In the specific example, the reconstructed time series is formed using diagonal averaging. However, alternative variations of the method 500*f* can implement another spectral estimation architecture having another decomposition and/or reconstruction algorithm.

Figure 6:
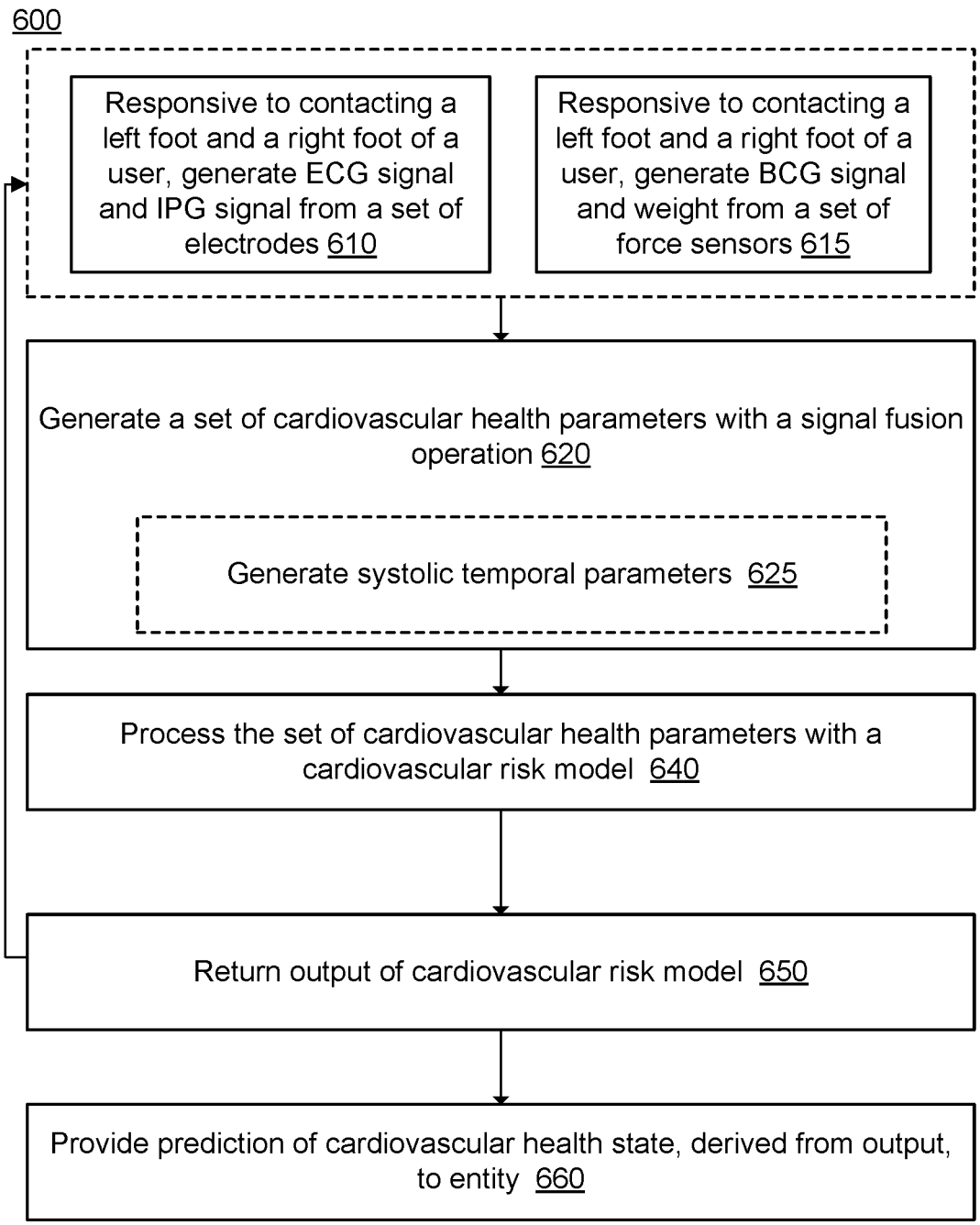
FIG. 6 depicts a flowchart of a method for electrical and mechanical cardiovascular signal acquisition processing, in accordance with one or more embodiments.

3. Method—Generation of and Fusion of Multiple Signals for Cardiovascular Health Monitoring FIG. 6 depicts a flowchart of a method 600 for electrical and mechanical cardiovascular signal acquisition processing, in accordance with one or more embodiments. As shown in FIG. 6, responsive to contacting the feet of the user, the array of electrodes generates 610 one or more electrical signals (e.g., ECG signals, IPG signals). Responsive to contacting the feet of the user, the set of force sensors also generate 615 one or more force-derived signals (e.g., BGC signals, a weight signal). Then, the computing subsystem (e.g., components of the electronics subsystem and/or the computing subsystem described above) generates 620 values of a set of cardiovascular health parameters, where generating values of a set of cardiovascular health parameters can include generating 625 values of systolic temporal parameters, several of which are described below. The computing subsystem then processes 640 values of the set of cardiovascular health parameters with a cardiovascular risk model, and returns 650 an output of the cardiovascular risk model.

The computing system can also provide 660 a prediction of the cardiovascular health state of the user, derived from the output, to an entity associated with the user. The entity can be another computing entity that provides further analysis of the prediction in relation to automated interventions for actively improving an undesired cardiovascular health state, or maintaining a desired cardiovascular health state. Automated interventions can be provided through medical devices (e.g., electrical stimulation devices, medication eluting devices, medication dispensing devices, etc.) in communication with the computing subsystem, such that the computing subsystem can also generate and/or provide instructions for controlling operation states of the medical device(s) for automated interventions. The entity can additionally or alternatively be a non-computing entity, such as a practitioner, emergency personnel, caretaker, family member, friend, or other acquaintance of the user.

The method 600 functions to process and fuse parameters derived from electrical signal(s) and force-derived signal(s) that are collected simultaneously or contemporaneously as a user steps onto a sensing surface, in order to extract values of cardiovascular health parameters. The parameter values can then be used to determine, in real time, a cardiovascular health state of the user. In one or more embodiments, systems associated with the method 600 generate ECG signals (e.g., such as in manners described above), IPG signals, BCG signals, and weight measurements through an interface with feet of a user. The method 600 and associated system components are configured such that the parameter values are regularly collected in a non-disruptive/non-invasive manner, and can be analyzed to monitor user cardiovascular health to trigger interventions at critical times, if needed.

The method 600 can be implemented by one or more portions of the system embodiment(s) described above, where portions of an array of electrodes (e.g., anterior, posterior, left, and right subportions of the array of electrodes) can provide electrical signals that are processed in different channels (e.g., ECG channels, IPG channels) and one or more force sensors can provide force-derived signals. The signals are then conditioned with electronics subsystem components and processed by computing subsystem to provide processed outputs that can be used to maintain or improve user health.

3.1 Method—Passive Electrical Signal Extraction

As shown in FIG. 6, responsive to contacting the feet of the user, the array of electrodes generates 610 one or more electrical signals.

Passive electrical signals, including the ECG signals described in relation to the method 500 above, can be generated. The passive electrical signals can thus include periodic signals generated by depolarization of the heart. The passive electrical signals can also include time varying components that include muscle activity information associated with muscles of the legs of the user and derived from electrical potentials produced by muscles used to stand and/or balance. The signals capturing leg muscle activity have a lower frequency due to contact impedance between the user's feet and the array of electrodes of the system. The signals capturing leg muscle activity are also modulated by changes in foot position, electrodermal activity of the skin, activity of sweat glands in the skin, and can be indicative of physiological and/or psychological arousal (in relation to autonomic nervous system activation).

3.2 Method—Active Electrical Signal Extraction

The same array of electrodes used to generate passive electrical signals can also generate active electrical signals, such as the IPG signals noted above, when the user steps onto the surface(s) in electrical contact with the array of electrodes; however, in alternative embodiments, IPG signals (or other electrical signals) can be collected with another set of electrodes. Each active electrical signal has a periodic component attributed to changes in resistance of the lower extremities as blood volume and flow changes with each heartbeat, and the periodic component (i.e., the IPG signal), is extracted by the computing subsystem and associated electronics with bandpass filtering (e.g., with a 0.5-30 Hz frequency band). Each active electrical signal also has a static or slow varying DC component that is representative of body impedance, and this DC component is indicative of water content in the body. The computing subsystem and associated electronics extract values of parameters from the DC component, where the parameters include one or more of: fluid status, extracellular and intracellular water content, body composition, body fat, and edema status. The periodic components and the DC components are derived at multiple frequencies by the computing subsystem, as described in more detail below, to extract additional information. For instance, a higher frequency signal (~64 kHz) can pass through more of the cell membranes in the body and thus represents overall body water content. A lower frequency signal (~8 kHz) less easily passes through cell membranes and represents extracellular water content. Thus, the computing subsystem can process signals at different frequencies to extract values of parameters related to total body water (TBW), extracellular water (ECW), and intracellular water (ICW) content.

In relation to active electrical signal generation, the system can provide a stimulation current that travels from one foot and through one leg of the user, and then through the other leg and the other foot of the user. The flow and presence of blood and other body fluids in the user's body presents a varying resistance to the stimulation current, where the resistance varies with fluid in a respective body region (e.g., a leg region) at any given time. The stimulation current encounters this change in resistivity which produces a detectable voltage change. In relation to a detectable voltage change, an active electrical waveform thus has characteristic peaks representative of the maximum and minimum fluid volume (e.g., blood volume) in a body region of the user associated with the stimulation current.

A subportion of electrodes used to generate the active signals can be configured to apply a stimulation current to the feet of the user through conductive aspects of the substrate described above. The stimulation current can be a small current (e.g., a current below 500 uA, a current below 1 mA, a current below 5 mA, a current below 10 mA, etc.). The stimulation current can also be a variable current with a regular waveform (e.g., sinusoidal waveform, non-sinusoidal waveform, square waveform, sawtooth waveform, etc.) or a non-regular waveform. However, the stimulation current can be non-variable, with known characteristics that can be used to assess body-region impedance. In one embodiment, the stimulation current is a current of approximately 500 uA having a frequency of 8-64 kHz.

In a configuration using paired electrodes associated with left and right sides of a device (and left and right sides of the body of the user), a first pair of electrodes can be used to apply the stimulation current, and a second pair of electrodes can be used to detect the active electrical signal(s). In relation to the device configuration shown in FIG. 2 above, the anterior electrodes can be used to apply the stimulation current, and the posterior electrodes can be used to detect the IPG signal(s). Alternatively, the posterior electrodes can be used to apply the stimulation current, and the anterior electrodes can be used to detect the IPG signal(s). Alternatively, with configured timing electronics architecture, the stimulation current can be applied with a pair of electrodes followed by detection of the IPG signal with the same pair of electrodes. Furthermore, in relation to timing electronics architecture, the electronics subsystem can implement timing operation modes for detection of the passive electrical signal(s) through the array of electrodes used to detect the active electrical signals.

3.3 Method—Force-Derived Signal Extraction and Other Signals

As shown in FIG. 6, responsive to contacting the feet of the user, the set of force sensors also generate 615 one or more force-derived signals (e.g., BGC signals, a weight signal). The set of force sensors and associated components of the electronics subsystem (e.g., analog circuitry) have a signal-to-noise ratio (SNR) and resolution sufficient for ballistocardiography, where the system detects small forces produced by physiological operation of the user's cardiovascular system (e.g., such as small perturbations of the body as the heart beats). Such forces can be associated with ejection of blood from the heart into the aorta (e.g., corresponding to a J-wave of a BCG signal), and travel of blood through the ascending and descending portions of the aorta to other portions of the user's body. BCG signals are extracted by the computing subsystem through bandpass filtering (e.g., of 0.5-50 Hz). A low frequency or DC component of the forced-derived signal is derived by the computing subsystem through lowpass filtering (e.g., with a cutoff frequency of 5 Hz), and characterizes motion of the user on the substrate as well as weight of the user standing on the device. In more detail, body weight can be extracted through summation of signals from all force sensors of the system, and motion can be extracted through lowpass filtering each force sensor independently and extracting center of pressure information.

During signal generation, additional sensors coupled to the electronics subsystem can also generate additional signals associated with the environment of the user. Such signals can include temperature signals and/or moisture signals, which can inform or affect other electrical signal measurements or force signal measurements. Additional sensors that can be implemented are described in more detail above.

3.4 Method—Cardiovascular and Other Physiological Health Parameter Extraction

Figure 7A:
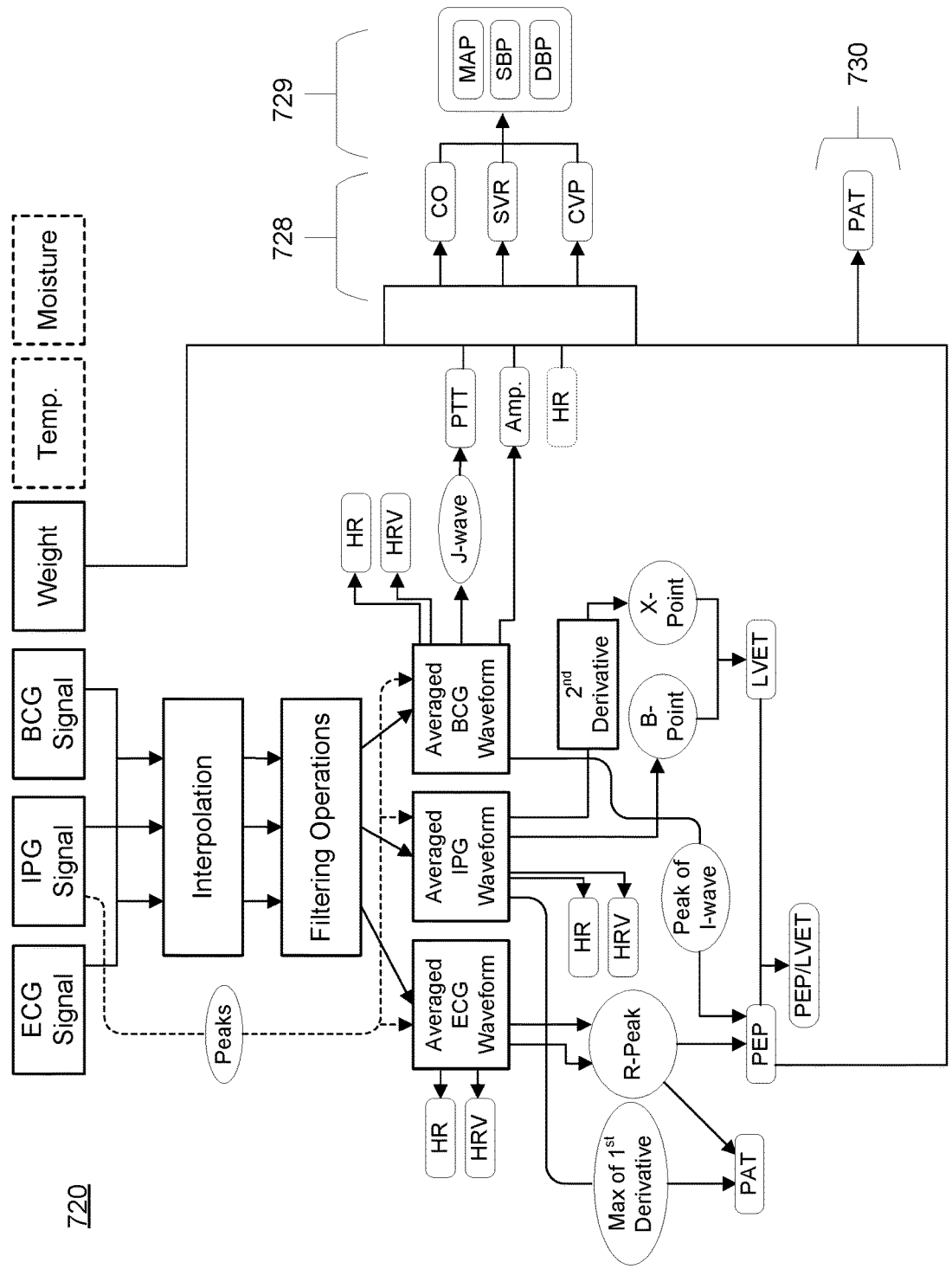
FIG. 7A depicts a flow diagram of cardiovascular health parameter extraction processes, in accordance with one or more embodiments.

FIG. 7A depicts a flow diagram of cardiovascular health parameter extraction processes, in accordance with one or more embodiments. As shown in FIG. 7A, the system generates one or more of (or one or more instances of, depending on sensor multiplicity and configuration): an ECG signal, an IPG signal, a BCG signal, a weight signal, a temperature signal, and a moisture signal. The electronics subsystem and/or computing subsystem then passes respective signals through different operation flows in order to extract values of parameters relevant to cardiovascular health, as described in more detail below in relation to FIGS. 7B-7G. Parameter values are then processed with a cardiovascular risk model in order to generate predictions of cardiovascular health state of the user, where the predictions can be used to trigger appropriate interventions to support the health of the user. The flows shown in FIGS. 7A-7G can be repeated regularly (e.g., multiple times a day, daily, weekly, etc.) whenever the user uses the device, where regular use is promoted by configuring elements of the system in a weighing scale form factor that can contemporaneously measure signals beyond weight signals. Regular measurements can thus provide rich data to longitudinally analyze cardiovascular health of the user.

The sensors of the system can also generate values of other physiological health parameters including galvanic skin potential, foot contact to electrodes, and foot-to-foot electromyography signals from passive electrical potentials; body water content (ECW, ICW, and TBW), body composition, and fluid status from active electrical signals; and body weight, center of pressure, and motion from force-derived signals. These parameters are used by the system to provide additional clinical context in a wide range of patient and user populations can are used by the system to detect noise and motion in the system, for noise mitigation and artifact removal, as described above and below.

3.4.1 Method—Ensemble Averaging

Figure 7B:
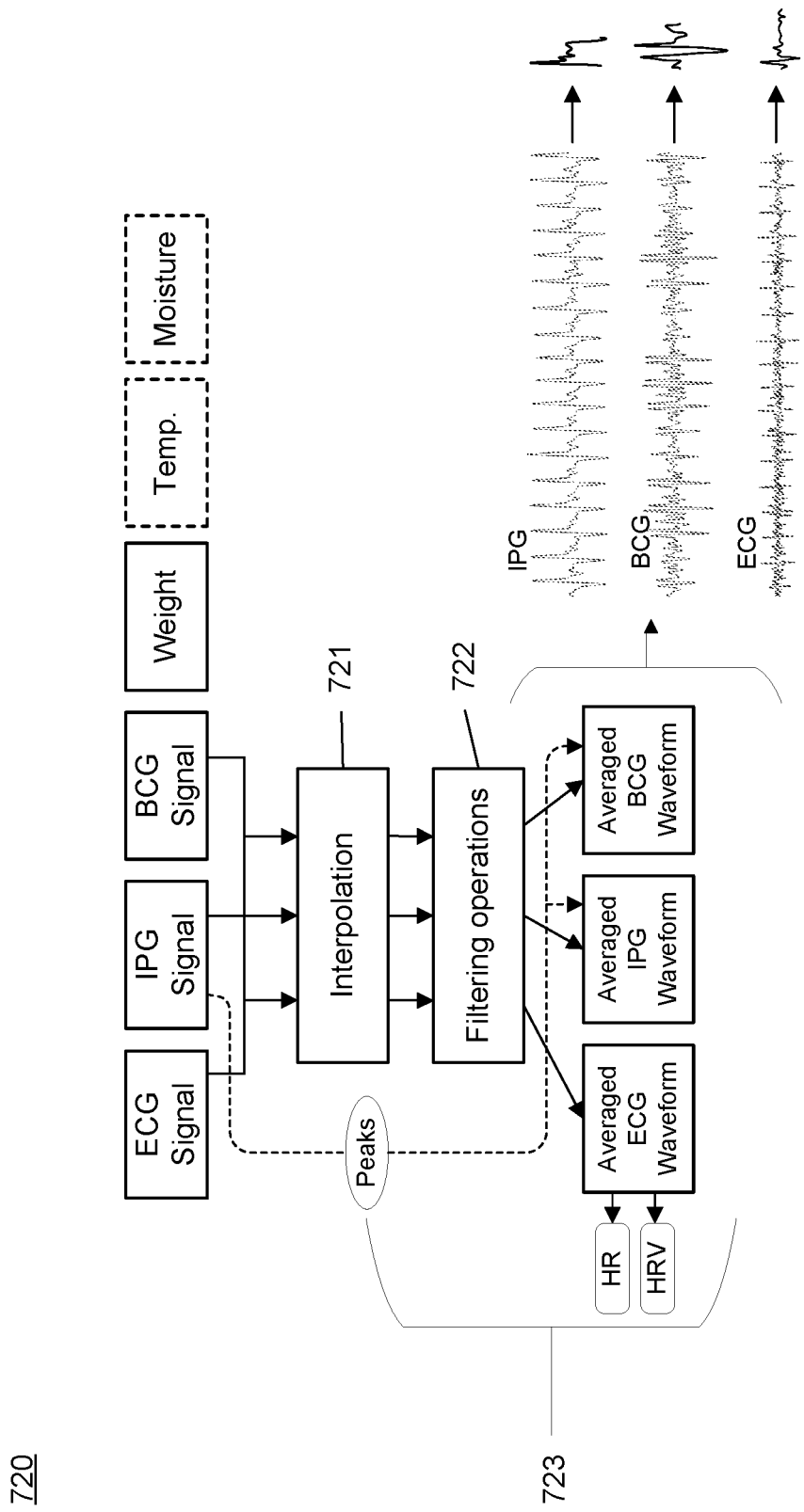
FIG. 7B depicts a first portion of the flow diagram shown in FIG. 7A.

FIG. 7B depicts a first portion of the flow diagram shown in FIG. 7A, which corresponds to an embodiment of a portion 620 of the method shown in FIG. 6. As shown in FIGS. 7A and 7B, the electronics subsystem, with associated computing architecture, can pass each of the ECG signal(s), the IPG signal(s) and the BCG signal(s) through an interpolation operation 721 and a set of filtering operations 722. In an embodiment, prior to interpolation and filtering, active and passive electrical signals are measured at 250 Hz sampling rate using a 24-bit delta sigma analog to digital converter (ADC) of circuitry of the system. In an embodiment, prior to interpolation and filtering, force-derived signals from each of the set of force sensors are sequentially sampled at 1 kHz using a 24-bit delta sigma ADC of circuitry of the system, where a higher sampling rate is associated with an increased number of force sensors.

As executed by the computing subsystem, in an embodiment, the interpolation operation can include interpolation of signals to 1 kHz in order to increase temporal resolution of the passive and active electrical signals, as well as force-derived signals. However, interpolation can be implemented by the computing subsystem with another suitable frequency of interpolation.

The filtering operations can include a bandpass filtering operation, as described above, and/or other filtering operations. The filtering operations can vary across different electrical signals and/or force-derived signals, and can include digital finite impulse response (FIR) techniques and/or infinite impulse response (IIR) techniques). In an embodiment, the filtering operations include a bandpass filter of 0.1-100 Hz for passive electrical signals associated with ECG signals. In an embodiment, the filtering operations include a bandpass filter of 5-100 Hz for passive electrical signals associated with leg muscle-derived electrical potentials. In an embodiment, the filtering operations include a bandpass filter of 0.5-30 Hz for active electrical signals associated with IPG signals. In an embodiment, the filtering operations include a bandpass filter of 0.5-50 Hz for force-derived signals associated with BCG signals. However, in variations, other frequency ranges can be used for different signal types, in different bandpass filtering operations.

Additionally or alternatively, the filtering operations can include a fourth-order high-pass filter operation followed by a low-pass filter operation. For each signal type, the high pass filter can include a cutoff frequency associated with higher-order derivatives of each signal type in order to preserver higher-order derivative features of the signal, where the cutoff frequencies can differ across signal type. However, the cutoff frequencies or frequency ranges can alternatively overlap. Similarly, the low pass filter can include a cutoff frequency associated with each signal type, where the cutoff frequencies differ across signal type. However, the cutoff frequencies or frequency ranges can alternatively overlap. In still other variations, the filtering operations can be applied to non-fourth order derivatives of the signal(s). Furthermore, the filter(s) can be applied to inbound signals in any other suitable order.

As indicated above, electrical and force-derived signals are sampled simultaneously when the user contacts the substrate with his/her feet, in order to facilitate extraction of cardiovascular health parameters that are reliant on phase relationships and accurate time synchronization between signals. As such, the system configuration enables automatic signal synchronization and accounts for misalignments due to filtering and other signal processing operations. However, in alternative embodiments, the system can collect different signals with non-simultaneous sampling, and implement signal registration and alignment techniques to extract cardiovascular health parameters that are reliant on phase relationships.

In relation to FIGS. 7A and 7B, the electronics subsystem, with associated computing architecture, can use an extracted feature of one signal type as references to ensemble average other signal types, with ensemble averaging techniques gated off a specific signal type. In embodiments described, the active and passive electrical signals, as well as dynamic force-derived signals, are small in magnitude and contaminated by noise and artifact, which motivates use of ensemble averaging. In embodiments described, the IPG signals have the highest signal-to-noise ratio (SNR), so characteristic feature(s) of the IPG signals are used to ensemble average each of the signals.

Figure 7C:
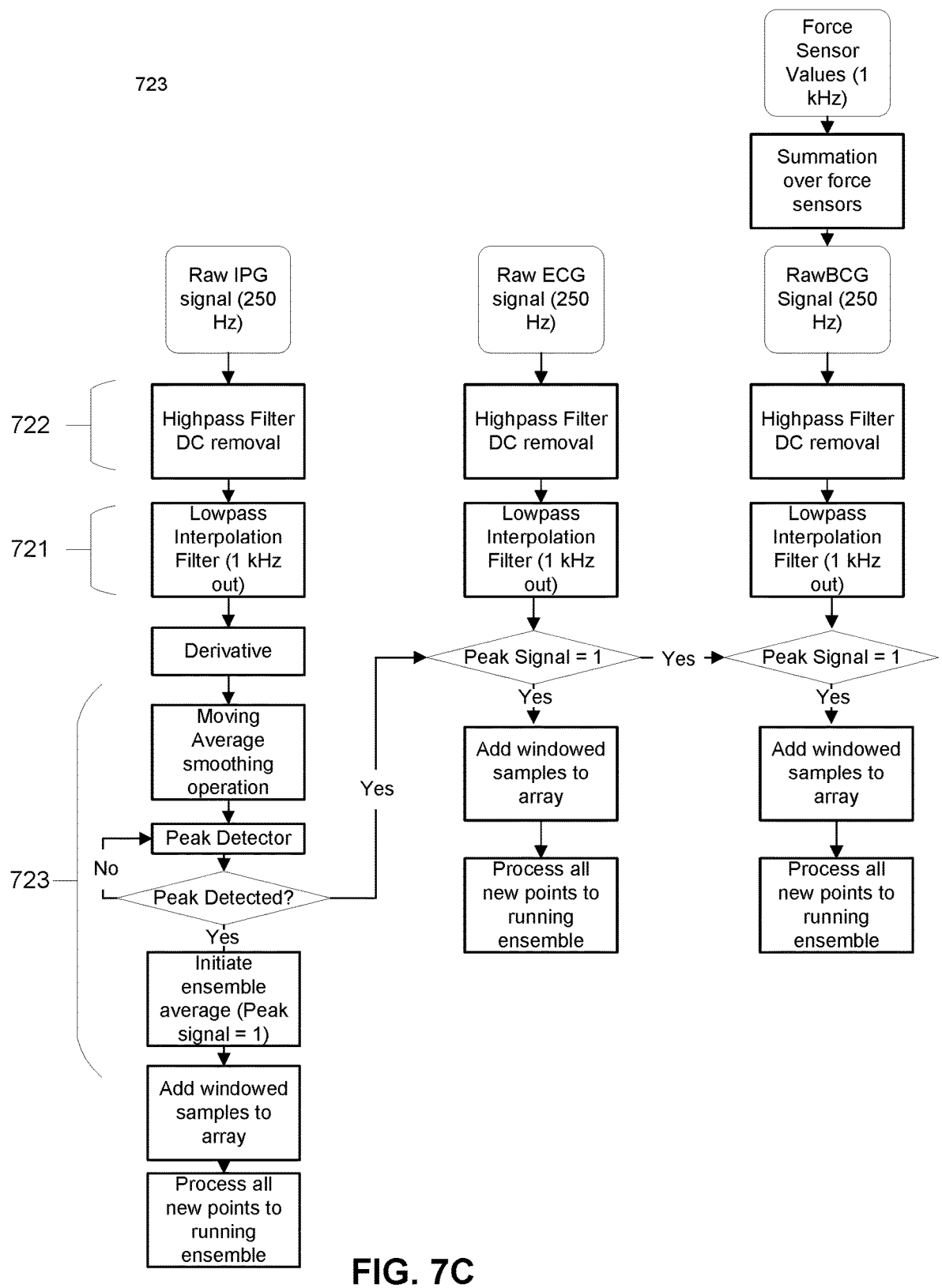
FIG. 7C depicts an expanded portion of the flow diagram shown in FIG. 7B.

In one embodiment, as shown in FIGS. 7A, 7B, and 7C, the computing subsystem can detect a set of peaks from the IPG signal, as the IPG signal is generated, and use the extracted peaks to generate 723 an ensemble averaged waveform for each of the ECG signal(s), the IPG signal(s), and/or the BCG signal(s). In more detail, the computing subsystem generates a first derivative of the IPG signal, smoothes the first derivative of the IPG signal with a moving average filter, and squares the output of the smoothing operation. The maximum peak of the IPG derivative signal is used as a gating feature for the ensemble averages of the processed electrical and force-derived signals. Each incoming peak of the IPG signal is then used as a temporal marker to collect and store a window (e.g., a window of 500-1000 ms) on each side of each temporal marker for each electrical and force-derived signal. As additional peaks are detected, windows of signals about each peak are summated and averaged to create ensemble averages of each signal type over a measurement period (e.g., associated with a session of a user standing on the substrate of the device). In this embodiment, the resulting ensemble averages result in approximately one heart beat cycle of information for each electrical signal and force-derived signal type. In various embodiments, however, the number of peaks over which an ensemble average is calculated can be adjusted by the computing subsystem to reduce noise, and in one embodiment, each ensemble average is generated over 20 heart beats. Averaging over a number (N) peaks is associated with a reduction in noise by a factor of the square root of N. In performing the ensemble averaging process 723, the computing subsystem can remove sources of noise that are non-periodic. For instance, an electromyography component (associated with lower limb muscle activation) of a passive electrical signal can overwhelm an ECG component of the passive electrical signal, and ensemble averaging using the IPG signal can remove non-periodic noise associated with the electromyography component.

In other embodiments, other features can be used to create the ensemble averages. For example, the computing subsystem can generate ensemble averages of signals based upon other IPG signal features (e.g., other maximum or minima), features of higher order derivatives of the IPG signal, and features of other transformations of the IPG signal. In still other embodiments, the computing subsystem can implement other non-IPG signals as the gating source(s) for ensemble averages. In one such embodiment, a BCG signal having sufficient quality can be processed by the computing subsystem to detect characteristic features (e.g., of an I-wave, of a J-wave) for use in ensemble averaging. Additionally or alternatively, in another embodiment, an ECG signal having sufficient quality can be processed by the computing subsystem to detect characteristic features (e.g., of a QRS peak) for use in ensemble averaging. The gating feature(s) can be constant across all users, or can be changed automatically and adaptively selected by the computing subsystem based characterization of quality of each signal type for each user.

3.4.2 Method—Noise Mitigation in Relation to Ensemble Averaging

Furthermore, in performing the ensemble averaging operation 723, the computing subsystem can use a weighted window process, whereby a variance-associated parameter (e.g., local variance, standard deviation) can be used to assign a weight to each signal window as it is processed to generate the ensemble average, where the weight decreases for a noisier signal window.

In related processes, in relation to noise mitigation using the ensemble averaging process, the computing subsystem blocks gating features from being further used in an ensemble averaging process, thereby blocking ensembling for windows of signals associated with high levels of noise or other artifacts. The computing subsystem can trigger blocking of gating features based upon comparison to a threshold noise condition. The computing subsystem can additionally or alternatively trigger blocking of gating features based upon another parameter value (e.g., center of pressure from force sensor-derived data, as a measure of motion). Threshold conditions for gating feature blocking can be constant for each measurement session, or can be adapted to each signal type. The computing subsystem also implements threshold condition comparisons in a manner that does not filter out features of interest (e.g., such as QRS complexes of ECG signals).

3.4.3 Method—Cardiovascular Parameter Extraction

Once signals have been measured and pre-processed, characteristic features and relationships between the signals are extracted by the computing subsystem to determine cardiovascular health states and/or other physiological states of the user(s). As described below, features of each of the IPG, ECG, and BCG signals can be extracted and co-processed to generate values of features correlated with cardiovascular health parameters.

Figure 7D:
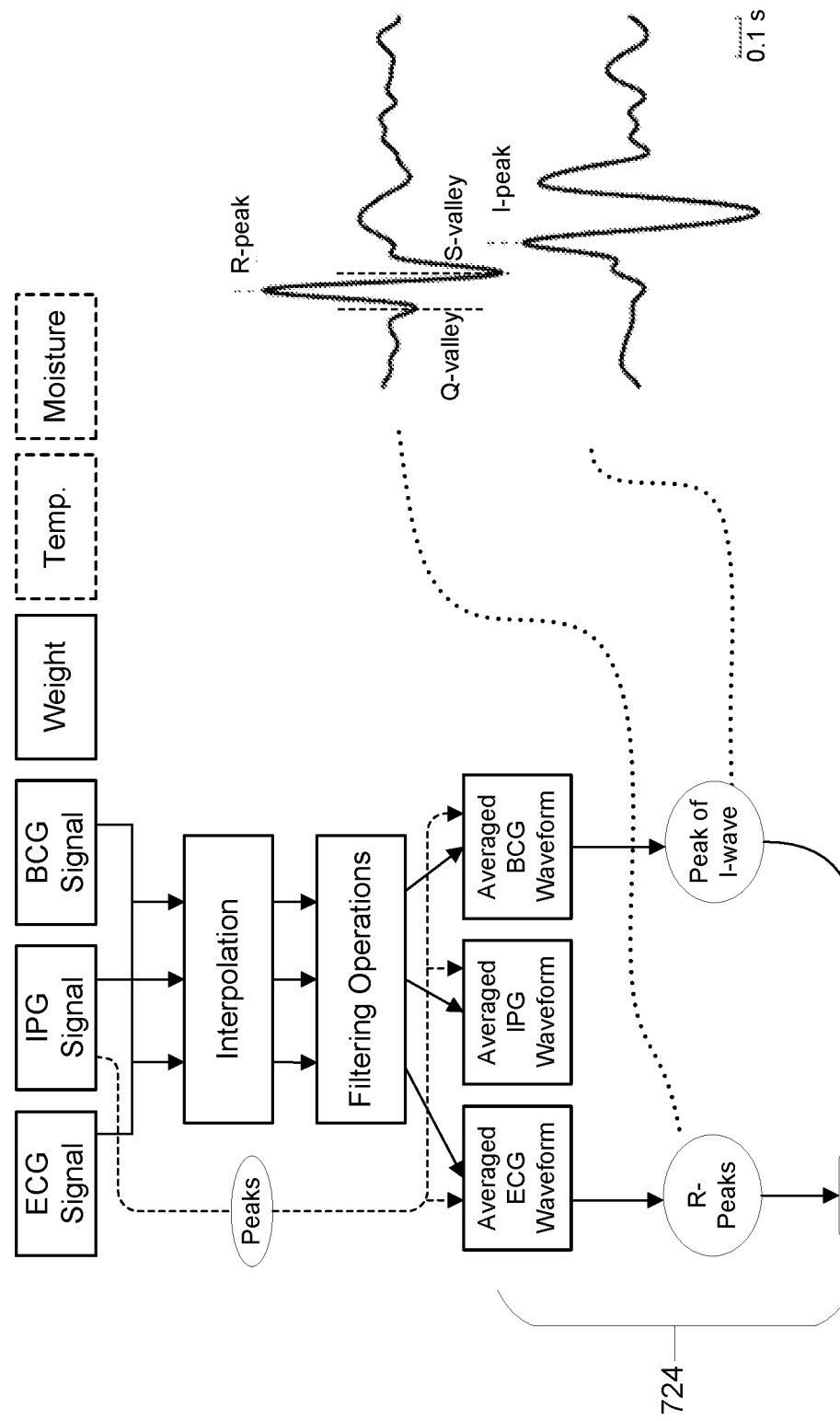
FIG. 7D depicts a second portion of the flow diagram shown in FIG. 7A.

FIG. 7D depicts a second portion of the flow diagram shown in FIG. 7A, which corresponds to an embodiment of a portion 620 of the method shown in FIG. 6. As shown in FIGS. 7A and 7D, the computing subsystem can identify an R-peak of an ECG signal or averaged ECG waveform and a peak of an I-wave of the BCG signal or averaged BCG waveform. The computing subsystem can then use the positions of the R-peak and the peak of the I-wave to extract 724 a pre-ejection period (PEP) for the user. The R-peak is a peak of the QRS complex corresponding to depolarization of the right and left ventricles of the heart, and captured in the ECG signal. The computing subsystem can use a wavelet analysis to identify the R-peak in the signal. The wavelet analysis can include a discrete wavelet transform to enhance the R-peak(s) in the ECG signal, followed by a peak finding process to find the time point associated with the R-peak. The I-peak can be a good proxy for the end of PEP, given that the I-wave represents a post-ejection of blood from the aorta, and the computing subsystem can use a peak finding process to locate the time point corresponding to a peak of the I-wave. The computing subsystem can then apply a correction operation to extract a more exact end of the PEP period, where the correction operation can be based upon modeling against a reference device that outputs a true value of PEP. Alternatively, the PEP and/or relative time points associated with the PEP can be estimated with a correction factor using other measured parameters, such as the pulse rate and/or pulse transit time. The correction operation can be universally applied to or alternatively customized to signals from different users (e.g., during different measurement systems). However, other features can be good proxies for locating an end of the PEP period (e.g., a B-point of an IPG-derived signal). The PEP characterizes a time between electrical depolarization of the heart and ejection of blood into the ascending aorta, which is related to a length of time the heart is contracting and reflects cardiac contractility.

Figure 7E:
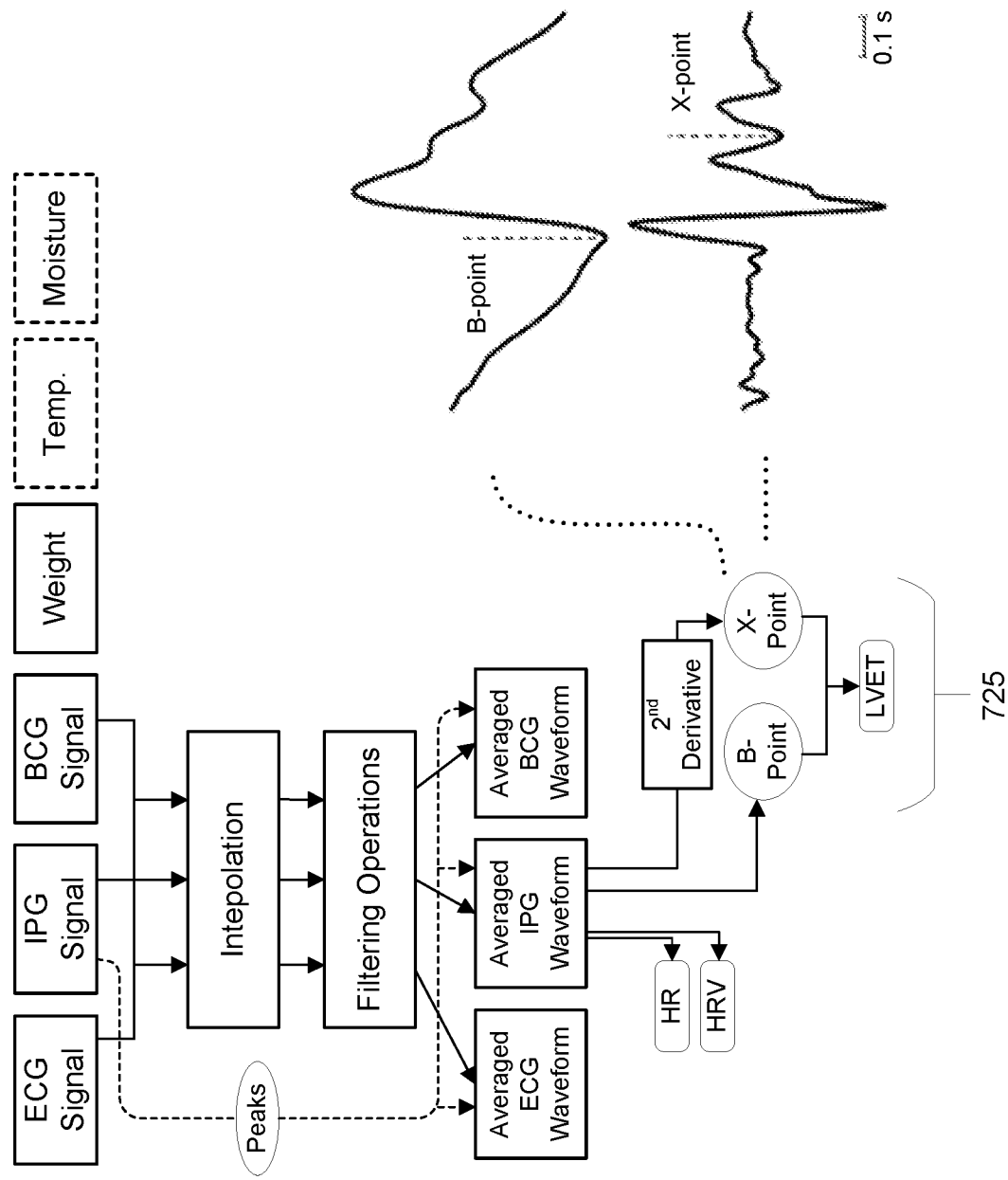
FIG. 7E depicts a third portion of the flow diagram shown in FIG. 7A.

FIG. 7E depicts a third portion of the flow diagram shown in FIG. 7A, which corresponds to an embodiment of a portion 620 of the method shown in FIG. 6. In an embodiment, the computing subsystem generates a first derivative of the average IPG waveform and applies a lowpass filter (e.g., of 15 Hz) to the first derivative. In an embodiment, the computing subsystem also generates a second derivative of the average IPG waveform and applies a lowpass filter (e.g., of 21 Hz) to the second derivative. In an embodiment, the computing subsystem also generates a third derivative of the average IPG waveform and applies a lowpass filter (e.g., of 21 Hz) to the third derivative. As shown in FIGS. 7A and 7E, the computing subsystem can identify a B-point of an IPG signal or averaged IPG waveform and an X-point from at least one of a first derivative, a second derivative, and a third derivative of the IPG signal or averaged IPG waveform. In particular, identification of one or more of the B-point and the X-point can be obscured by noise or atypical signal morphology. As such, one or more of the other signals (e.g., ECG-derived signals, BCG-derived signals, IPG-derived signals) can be used to correctly identify B and/or X-points. For instance, the R-peak of an ECG-derived signal can be used to define a physiological window in which the B-point is expected to be found. As such, other signals can be used to generate physiologically relevant time windows where other signal features are expected to be found, in order to improve localization of such features. The computing subsystem can then determine 725 the left ventricular ejection time (LVET) for the user from the time distance between the B-point and the X-point, where the LVET is a time period of blood flow across the aortic valve, as influenced by the heart rate (HR) of the user, the pre-load on the aortic valve, the afterload on the aortic valve, and contractile state. In more detail, in determining the LVET for the user, the computing subsystem can generate a second derivative of the averaged IPG waveform (or IPG signal) and identify a first minimum immediately preceding a maximum change in impedance in the averaged IPG waveform (or IPG signal), where the time point associated with the first minimum corresponds to the B-point. The computing subsystem can also identify an absolute minimum of the second derivative of the averaged IPG waveform (or IPG signal), where the time point associated with the absolute minimum corresponds to the X-point. Then, the computing subsystem can determine left ventricular ejection time (LVET) from positions of the first minimum and the absolute minimum.

In a related embodiment, the LVET can be determined from features of BCG-derived signals and/or IPG-derived signals. For instance, a BCG-derived signal can be high-pass filtered and/or derivatives of the BCG-derived signal can be calculated, such that higher frequency components of the signal are emphasized and extracted. The resulting features can represent vibrations of the user's body due to the aortic valve opening and closing, and can be used by the computing subsystem to determine temporal markers representative of the opening and closing of the valves. These temporal markers are then used, with or without combination of IPG-derived features, to calculate the LVET for a user. These features can also be used with ECG-derived features to calculate PEP. For instance, the computing subsystem can process an R-peak time point and a time point of an aortic valve opening feature of a BCG-derived signal to determine PEP.

As such, transformations on ensemble average signals can be used to extract features, where derivatives and higher order derivatives (e.g., second derivatives, third derivatives, fourth derivatives, etc.) of an averaged ensemble signal (e.g., averaged IPG signal) can be used to extract features (e.g., peaks and valleys) associated with different cardiovascular time intervals. Furthermore, time intervals associated with transformations of a signal can be used to extract derivative features.

The computing subsystem can extract amplitude features from the ensemble averaged signals. In particular, because ensembling involves gating, small changes in timing and phases of the signals during a measurement session across different signal types can result in a reduction in feature amplitudes for signals that do not contain the gating feature. Thus, the computing subsystem can recover true amplitudes of features in each signal type by realigning each individual ensemble averaged waveform using its individual component signals. In one example, to realign a BCG signal, the J-wave of each component signal used to generate the ensemble averaged BCG signal can be used to realign the ensemble components. Since the J-wave location is known, a tighter window (e.g., window less than 500 ms) can be used to detect local peaks associated with the J-wave location, and used to realign the ensemble components. Then, after realignment, the true amplitude of the J-wave components can be extracted by the computing subsystem.

Figure 7F:
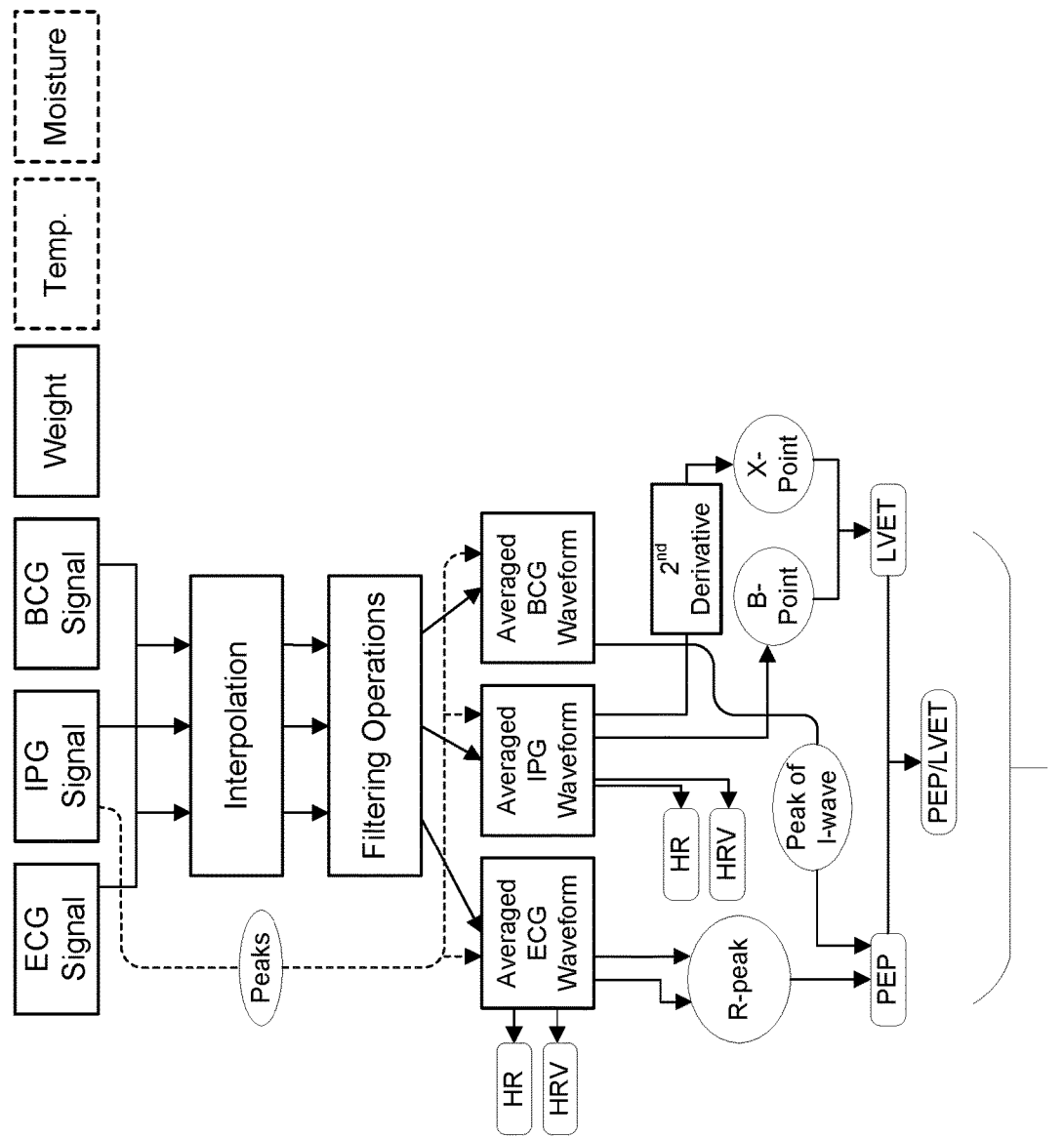
FIG. 7F depicts a fourth portion of the flow diagram shown in FIG. 7A.

FIG. 7F depicts a fourth portion of the flow diagram shown in FIG. 7A, which corresponds to an embodiment of a portion 620 of the method shown in FIG. 6. As shown in FIGS. 7A and 7F, the computing subsystem determines a PEP/LVET ratio derived from signal fusion processes applied to the ECG signal and the IPG signal, where the PEP and LVET for the user can be determined as described in relation to FIGS. 7C and 7E above. The PEP/LVET ratio characterizes an index of left ventricular systolic performance (i.e., systolic time ratio, STR) that is correlated with ejection fraction, which is a measurement of the fraction of blood leaving the heart of the user each time it contracts. In particular, a PEP/LVET ratio that is above a threshold value can be used by the computing subsystem to diagnose a patient with systolic heart failure. For example, a PEP/LVET ratio greater than 0.40 (or another threshold) can indicate that a patient has an ejection fraction less than 40% (or another value). The computing subsystem can also use the PEP/LVET ratio to phenotype patients. For instance, the PEP/LVET ratio can be used to discriminate between the two most common forms of heart failure (e.g., reduced ejection fraction-associated heart failure and preserved ejection fraction-associated heart failure).

Figure 7G:
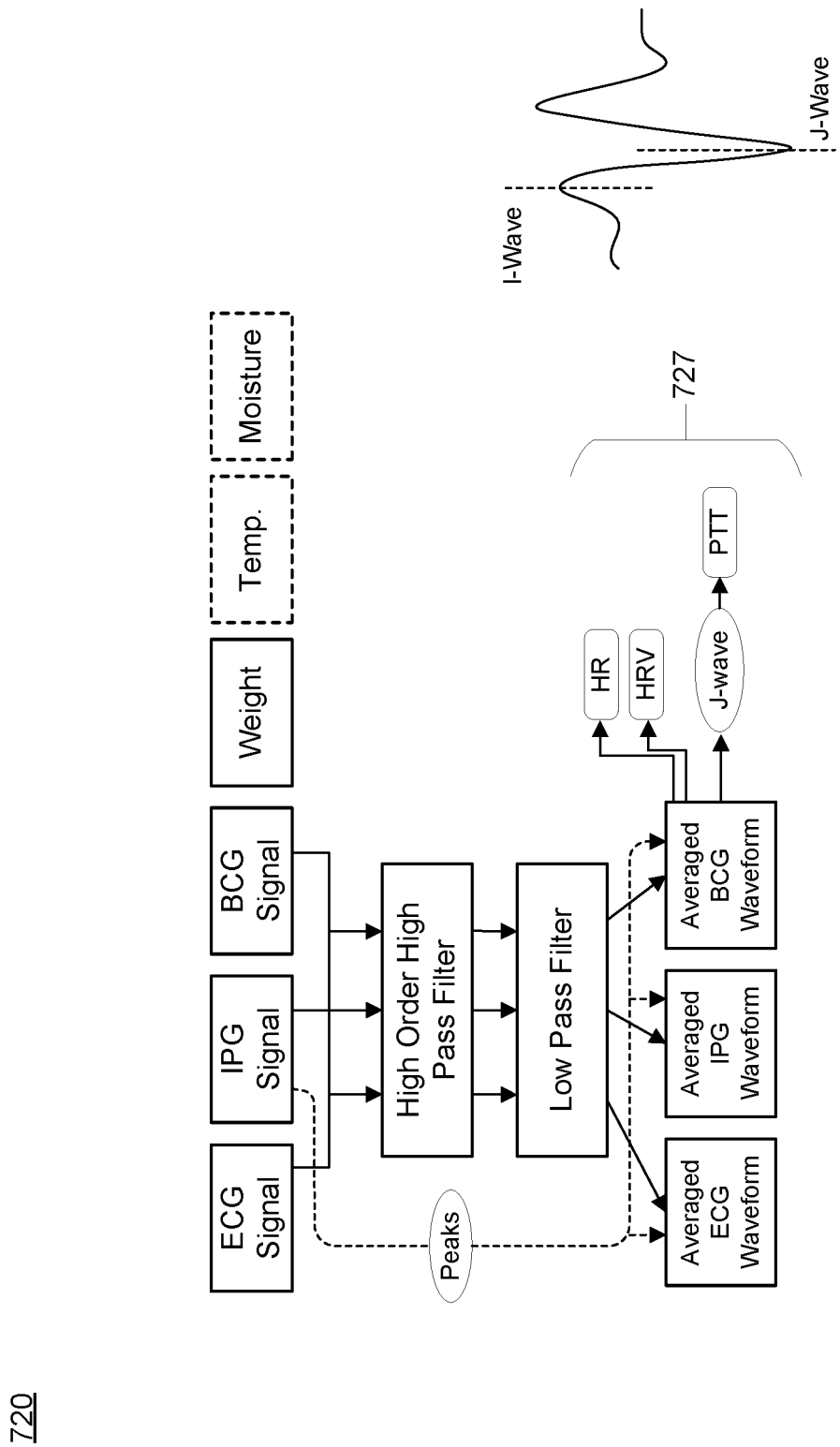
FIG. 7G depicts a fifth portion of the flow diagram shown in FIG. 7A.

FIG. 7G depicts a fifth portion of the flow diagram shown in FIG. 7A, which corresponds to an embodiment of a portion 620 of the method shown in FIG. 6. As shown in FIGS. 7A and 7G, the computing subsystem identifies a J-wave position of the averaged BCG waveform (or BCG signal), where the J wave corresponds to a deflection in a signal between a QRS complex of a cardiac phase and an ST segment of a cardiac phase. The computing subsystem can then detect an arrival time of a pulse associated with the J-wave at least at one of the left and the right foot of the user, through the set of force sensors of the system. Then, based upon the time point corresponding to the J wave position, the arrival time of the pulse, and a height of the user, the computing subsystem can generate 727 a pulse transit time (PTT) and/or pulse wave velocity (PWV) for the user. In more detail, the computing subsystem determines the PTT and the PAT from multiple signals, where, in one embodiment, the PTT is calculated using an IPG-derived signal and a BCG-derived signal. In more detail, a peak of the I-wave is used as a first temporal maker, and a maximum value of the IPG-derived signal is used as a second temporal marker, where the distance between the first and the second temporal markers is equal to the PTT. However, other features of the IPG and/or BCG-derived signals can be used to determine PTT. For example, the J-wave peak and the X-point of the IPG-derivative can be used to determine the PTT, the B-point of the IPG-derivative and the J-wave of the BCG-derived signal can be used to determine PTT, the I-wave peak of the BCG-derived signal and the X-point of the IPG-derivative can be used to determine PTT, and/or the I-wave peak of the BCG-derived signal and the maximum peak of the IPG-derivative can be used to determine PTT.

The PTT characterizes the time it takes for a pulse pressure waveform to travel along a portion of an arterial tree (e.g., from the aortic arch to a lower torso region of the user), and the PWV characterizes a speed of travel of the pulse pressure waveform. The computing subsystem can also locate an I-peak of the averaged BCG waveform, as shown in FIG. 7G, by implementing a peak finding algorithm in relation to the J-wave position. The computing subsystem can then use the position, amplitude, or other aspect of the I-peak to derive systolic temporal parameter values or other parameter values related to health risk.

FIG. 7A also depicts a portion of a method where the computing subsystem fuses signals of multiple types to extract one or more of: a mean arterial pressure, systolic blood pressure (SBP), and a diastolic blood pressure (DPB) for the user. In more detail, the computing subsystem identifies a pulse rate from at least one of the averaged ECG waveform, the averaged IPG waveform, the averaged BCG waveform, and the ensemble waveform. In an embodiment, the pulse rate can be determined from peaks of the IPG signal, and a heart rate ensemble averaged signal can be generated with a windowing operation, as described above (e.g., with a window of −1500 to 500 ms about respective peaks in the IPG signal). The computing subsystem then identifies a BCG amplitude from the averaged BCG waveform. Then, the computing subsystem transforms 728 the PEP (determined as described above), the PTT (determined as described above), the pulse rate, the BCG amplitude, and a user weight derived from the weight signal into a cardiac output (CO) value, a systemic vascular resistance (SVR) value, and a central venous pressure (CVP) value. Finally, with the CO, SVR, and CVP values, the computing subsystem determines 729 a mean arterial pressure (MAP) for the user from a product of the cardiac output (CO) value and the systemic vascular resistance (SVR) value added to the central venous pressure (CVP) value.

In relation to pulse rate, the computing subsystem can determine pulse rate in real time from any one or more of ECG-derived signals, IPG-derived signals, and BCG-derived signals. The computing subsystem can additionally or alternatively determine pulse rate (i.e., average pulse rate determined over the course of a measurement session) from one or more averaged waveforms (i.e., averaged ensemble signals). For instance, if the window for an ensemble operation is extended (e.g., to approximately 2× or longer than the period of an average pulse), the computing subsystem captures multiple heart beats in a given ensemble. The average pulse rate can then be derived by detecting time points of instances of a characteristic feature (e.g., peak of an IPG-derived signal, R-peak of an ECG signal) across each waveform period used to generate a final ensemble, where the difference between the time points is used to calculate pulse rate. In this embodiment, the determined pulse rate only encompasses beats that were included in the determination of a respective ensemble averaged waveform, and is robust in relation to low-quality and/or low resolution signals. Furthermore, if certain features are blocked (by the filtering operations described) due to motion or other artifacts associated with a measurement, the features are automatically removed from consideration during generation of an ensemble averaged waveform and also pulse rate determination. Thus, the pulse rate can be robustly determined from generating an ensemble averaged waveform of one or more of the ECG signal, the IPG signal, and the BCG signal.

In relation to previously described parameters, the computing subsystem, as shown in FIG. 7A, also further generates 730 a pulse arrival time (PAT) for the user from a summation of the PEP (determined as described above) and the PTT (determined as described above). Additionally or alternatively, PAT can be determined as inferred from the ECG-derived signals, the BCG-derived signals, and the IPG-derived signals. For instance, the PAT can be determined by the computing subsystem based on the R-peak of the ECG-derived signal and a maximum of the first derivative of the IPG-derived signal.

Furthermore, in some embodiments, physiologically-relevant time intervals (e.g., PEP and LVET) determined by the computing subsystem are influenced by pulse rate. As such, the computing subsystem can also correct these physiologically-relevant time intervals based on the pulse rate determination so that their physiological significance is properly assessed (e.g., in relation to generation of appropriate interventions). In one example, a corrected $LVET_c$ can be generated based on the formula $LVET_c=1.5*HR+LVET$, where HR is the pulse rate. In one example, a corrected $PEP_c$ can be generated based on the formula $PEP_c=0.4*HR+PEP$. The corrected time intervals (e.g., $PEP_c$, $LVET_c$) can be determined from real-time ECG, BCG, and/or IPG signals, and/or with generation of ensemble averaged waveforms (as described above), where corrected and uncorrected time intervals can be used as inputs to predictive models (e.g., predictive models of cardiovascular health risk described in relation to FIG. 8 below). For instance, the PEP/LVET ratio can be determined using corrected intervals (e.g., $PEP_c/LVET_c$), as described above.

Figure 7H:
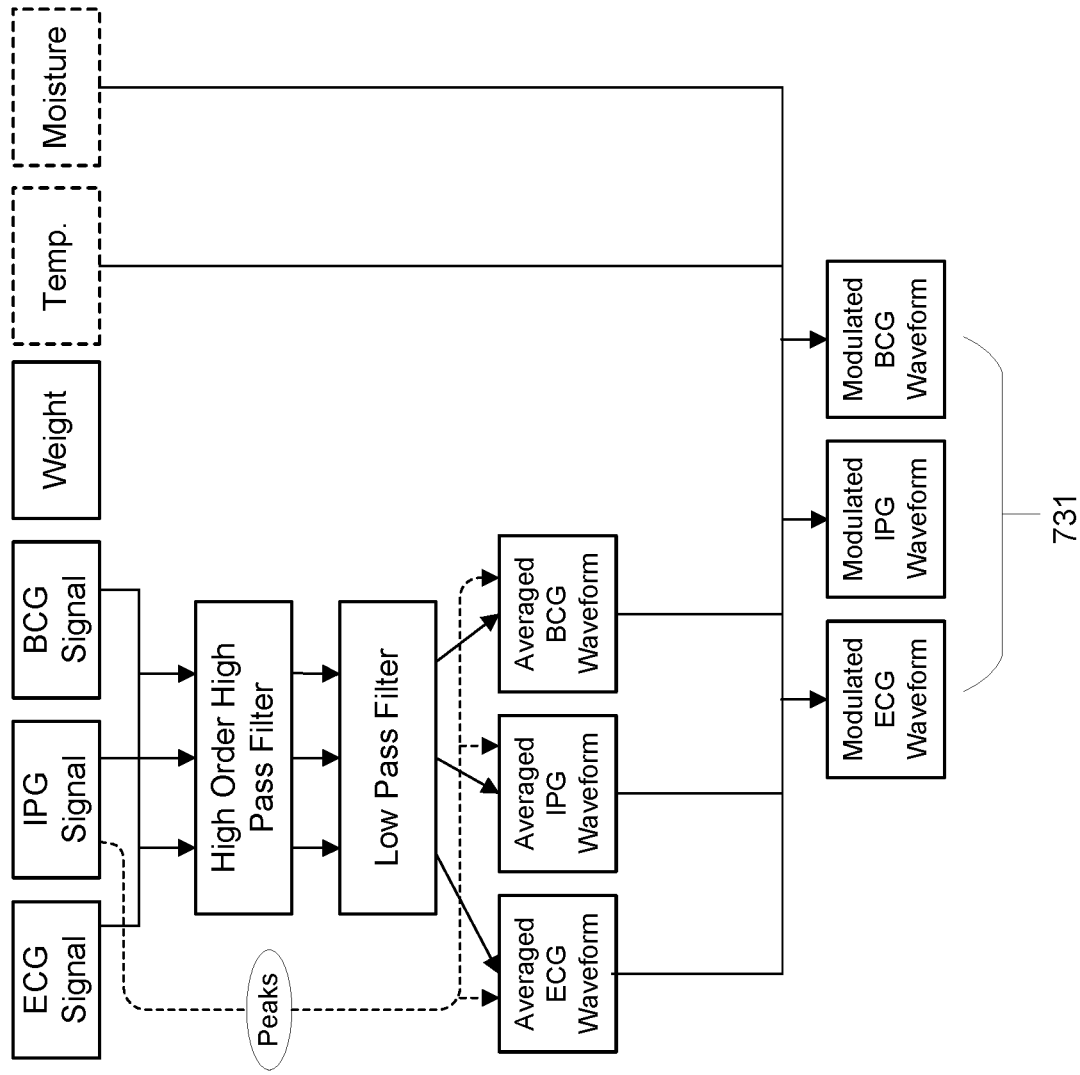
FIG. 7H depicts a sixth portion of the flow diagram shown in FIG. 7A.

FIG. 7H depicts a sixth portion of the flow diagram shown in FIG. 7A, which corresponds to an embodiment of a portion 620 of the method shown in FIG. 6. As shown in FIGS. 7A and 7G, the computing subsystem modulates 731 one or more of the averaged ECG waveform, the averaged IPG waveform, and the averaged BCG waveform with input temperature signals from the temperature sensor and/or moisture signals from the moisture sensor described in relation to the system above. As such, responsive to contact the left foot and the right foot of the user, the computing subsystem can generate a temperature signal and a humidity signal and modulate a value of at least one of the set of systolic temporal parameters based upon the temperature signal and the humidity signal. For instance, the computing subsystem can modulate operation due to device changes (e.g., changes in electrode resistance due to changes in humidity) and/or physiological changes of the user due to excessive heat and/or humidity.

Also in relation to the system described above, the computing subsystem can calculate body impedance, which is correlated with body water content, from the electrical signals generated. The computing subsystem can also determine balance of the user as the user steps onto the substrate, where the balance analysis can include one or more of: movement in multiple directions (e.g., lateral directions, anterior/posterior directions), center of pressure, postural sway, sway path, sway velocity, balance index, and any other suitable components of the user's balance.

Furthermore, in some embodiments, any derived parameters (e.g., MAP, SV, CO, systolic time intervals, etc.) can be absolute measurements or relative measurements (e.g., compared to a baseline or other reference measurement). Relative and/or absolute measurements can be calibrated against a reference device for improved accuracy. For example, a derived stroke volume model can be calibrated for a specific user by collecting data from a reference device (e.g., a device operating according to the Fick method, thermodilution device, impedance cardiography device, etc.) contemporaneously with collection of data from an embodiment of the system described above, in order to improve accuracy in the values of the parameters determined from the embodiment of the system described above.

Figure 8:
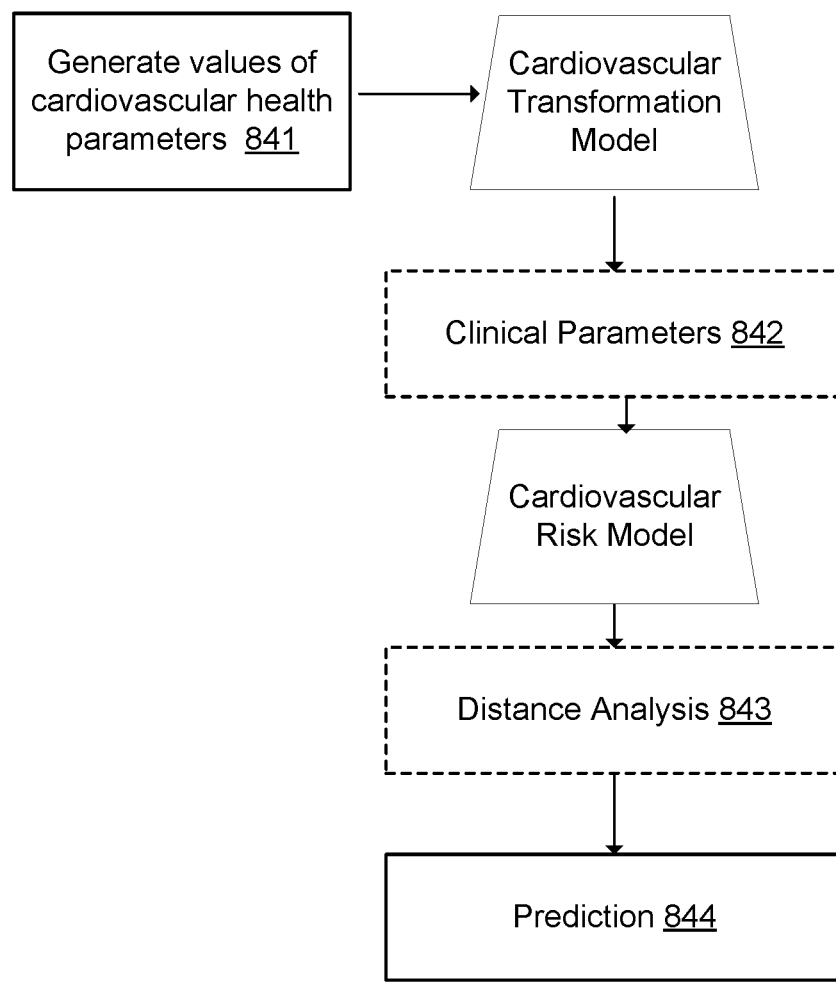
FIG. 8 depicts a flowchart of a method for processing cardiovascular health parameters with a risk model, in accordance with one or more embodiments.

4. Method—Processing Cardiovascular Health Parameter Values with Risk Model and Generating Predictions of Cardiovascular Health State FIG. 8 depicts a flowchart of a method for processing cardiovascular health parameters with a risk model, in accordance with one or more embodiments. As shown in FIG. 8, the computing subsystem generates 841 values of cardiovascular health parameters during each measurement session for a user, as described above. In embodiments, as described above, the computing subsystem generates time interval and amplitude-derived features. These features are used to build models of clinical parameters associated with cardiovascular health risks. The computing subsystem can thus transform 842 values of time interval and amplitude-derived features into clinically relevant parameters, including stroke volume, cardiac output, blood pressure, system vascular resistance, and other parameters. The clinical parameters can then be input into trained risk models configured for generating predictions of cardiovascular health states of the user(s), where cardiovascular health states can be related to stable states, worsening states (e.g., of various forms of heart disease), and/or indeterminate states. In one example, outputs of the cardiovascular risk model for a particular user can be processed with a distance analysis 843 or another analysis that compares parameters for a particular user to outputs of the model associated with cardiovascular health states. The computing subsystem can then use the distance analysis or another analysis to return a prediction 844 of the cardiovascular health state of the user. In an example, the prediction can indicate decompensation in a heart failure patient and the computing subsystem can use the prediction to drive remote interventions (e.g., for reduction of unnecessary hospitalizations).

Additionally, the computing subsystem can include architecture for predicting and generating models of disease phenotypes (e.g., disease phenotypes of heart failure between systolic and diastolic variants). In another example, the computing subsystem can transform stroke volume inputs, systemic vascular resistance inputs, and impedance inputs into a hypertension phenotype. Such phenotypes can be used by the computing subsystem to order to identify if a user is suffering from a fluid status issue or a blood volume issue. As described in relation to intervention provision below, phenotyping can subsequently be used to more precisely administer the therapy targeting at underlying mechanisms of undesired health states.

In relation to generating parameter values and processing parameter values with models, the computing subsystem can process combinations of cardiovascular and other physiological parameters generated according to methods described above, in order to generate predictions. For instance, the computing subsystem can use weight and baseline impedance parameters to generate an index of fluid status in addition to generation of outputs related to cardiac status. The combination of fluid status and cardiac status information can be used by the computing subsystem to augment sensitivity and specificity for certain conditions where, for instance, fluid status changes (e.g., related to fluid retention) in association with cardiac status changes (e.g., related to deterioration in state) can indicate statuses (e.g., related to heart failure, related to chronic obstructive pulmonary disease, related to chronic kidney disease, etc.) with increased sensitivity and specificity. Furthermore, combination of weight information, impedance information, and other cardiac data can be used by the computing subsystem to determine dry weight (i.e., the normal weight of a patient's body without any fluid accumulation). In more detail, the computing subsystem can determine dry weight upon assessing fluid status in combination with simultaneous measures of hemodynamic performance (MAP, CO, systolic time intervals, etc.). Dry weight assessment is important in relation to conditions (e.g., heart failure, kidney disease, etc.), where changes in fluid can be measured relative to a dry weight baseline. Furthermore, effective diuresis benefits from knowledge of a user's dry weight.

In another example, the computing subsystem can generate model outputs based on body weight to improve a user's cardiac status in an actionable feedback loop. In more detail, if a user is determined to have high blood pressure due to excessive body weight, the computing subsystem can generate an associated prediction and generate intervention protocols (e.g., a weight loss program, control instructions for an exercise regimen administered by connected exercise equipment, control instructions for a connected dispenser containing weight loss supplements, etc.) for the user. The interventions can also include tailored modifications to operation of the systems described above, where the system measures body weight and cardiac status for the user simultaneously and provides such information to the user or another associated entity to promote improvements to health statuses of the user. In more detail, simultaneous measurement of weight, in combination with height information (e.g., as input by the user or another entity, as determined in another manner) can be used by the computing subsystem to generate indices of cardiovascular function normalized to the user's body type (e.g., in terms of BMI, body surface area, or other derivative measures of body type). In an example, stroke volume and cardiac output can be calculated and transformed into a stroke index and a cardiac index, respectively, by dividing stroke volume and cardiac output by body surface area (as determined from height and weight using the Du Bois formula, using a Haycock method, etc.). In particular, cardiac index is a hemodynamic parameter that relates the cardiac output (CO) from the left ventricle in one minute to body surface area, and thus relates heart performance to a size of a user.

Figure 9:
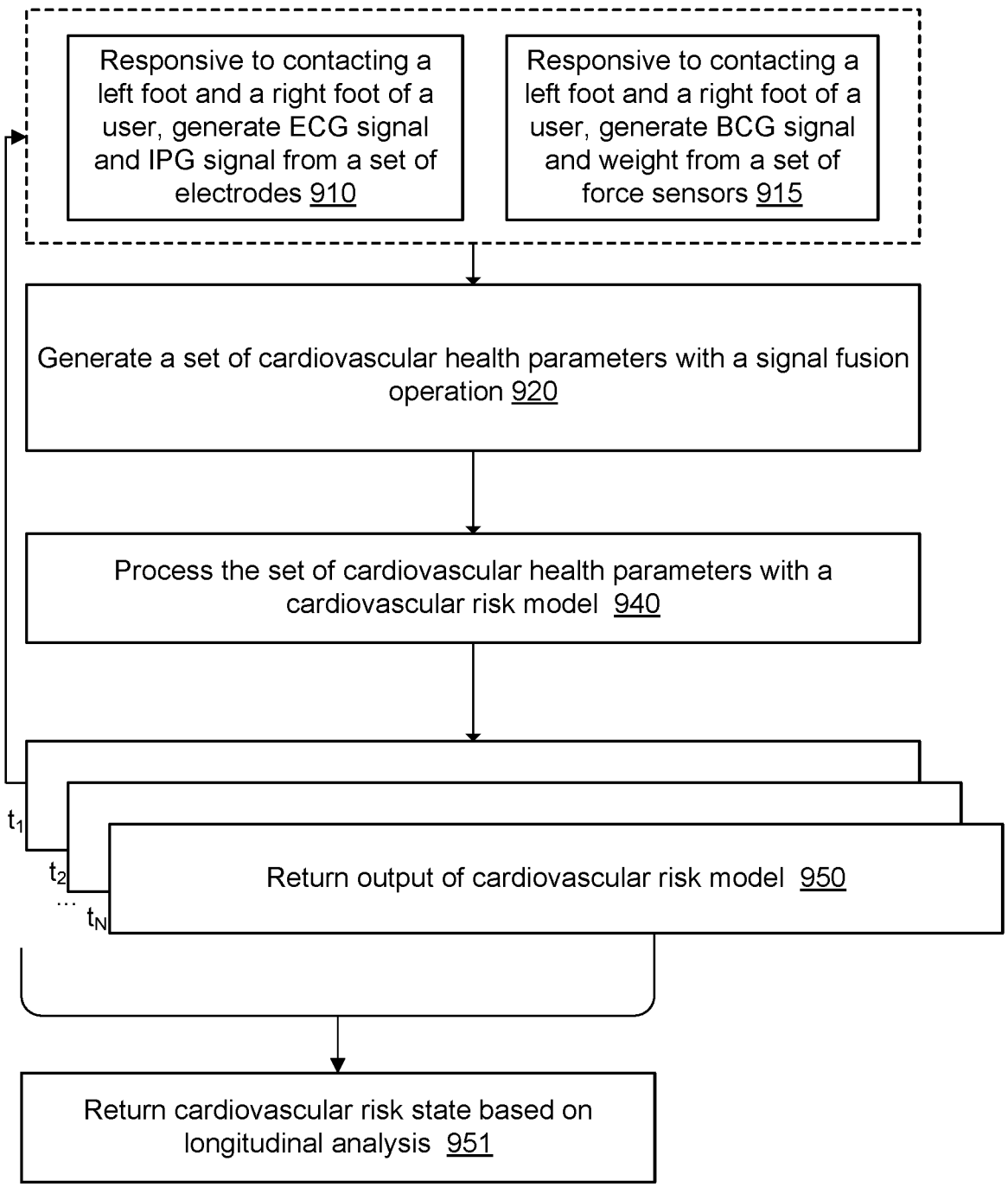
FIG. 9 depicts a flowchart of longitudinal monitoring of cardiovascular health of a user, in accordance with one or more embodiments.

FIG. 9 depicts a flowchart of longitudinal monitoring of cardiovascular health of a user, in accordance with one or more embodiments. As shown in FIG. 9, responsive to contacting the feet of the user, the system can generate 910 passive and active electrical signals (e.g., ECG and IPG signals) from a set of electrodes, according to embodiments described above. Responsive to contacting the feet of the user, the system can also generate 915 force-derived signals (e.g., weight signals and BCG signals), according to embodiments described above. The computing subsystem can then generate 920 a set of cardiovascular health parameters with a signal fusion operation according to embodiments derived above, where the cardiovascular health parameters are processed 940 by the computing subsystem with a risk model. The computing subsystem can the return outputs 950 of the cardiovascular risk model at multiple time points associated with different measurement sessions for the user. The outputs associated with different time points can be processed 951 with a longitudinal analysis, in order to generate insights into changes in the user's health condition over time. Longitudinal analyses can be used to promote interventions that are more tailored to the user's specific condition. For instance, the computing subsystem can generate instructions for automatic medication adjustments for a user. In one specific example, the computing subsystem's outputs can be used for automatic titration of diuretic dosing for a heart failure patient. In other examples, automatic medication adjustment, as determined using outputs of the computing subsystem, can be applied to other chronic disease conditions (e.g., hypertension).

4. Conclusion

The system and method(s) described can confer benefits and/or technological improvements, several of which are described herein. For example, the system and method(s) can produce fused or composite data that characterize complex physiological behavior, which is analyzed to provide insights into improving user health interventions. Such data structures and processing methods can be used to efficiently generate comparisons across a large amount of data from different sources, for a large number of users over time.

The system and method(s) can further employ non-typical use of sensors. For instance, the system and method(s) can employ sensor arrays including different types of sensors in a spatial and structural configuration that enables significant improvements in increasing SNR for extremely noise biometric signals taken from non-traditional body regions. As such, the system and method(s) can provide several technological improvements.

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A method for electrical signal processing comprising:
   generating, from an array of electrodes distributed across a plane:
      an electrocardiogram (ECG) signal from a left subportion and a right subportion of the array of electrodes, the left subportion and the right subportion forming, during use, a circuit across an inferior sagittal plane of a user;
      a first noise signal from the left subportion of the array of electrodes, wherein generating the first noise signal comprises generating the first noise signal from a left anterior electrode and a left posterior electrode of the left subportion of the array of electrodes;
      a second noise signal from the right subportion of the array of electrodes, wherein generating the second noise signal comprises generating the second noise signal from a right anterior electrode and a right posterior electrode of the right subportion of the array of electrodes; and
   generating a de-noised ECG signal upon processing the ECG signal with at least one of the first noise signal and the second noise signal.

2. The method of claim 1, wherein generating the ECG signal comprises generating the ECG signal from a left anterior electrode of the left subportion and a right anterior electrode of the right subportion.

3. The method of claim 2, wherein generating the ECG signal further comprises generating the ECG signal from a left posterior electrode of the left subportion and a right posterior electrode of the first subportion.

4. The method of claim 1, wherein generating the de-noised ECG signal comprises performing an adaptive filtering operation on the ECG signal and a summation of the first noise signal and the second noise signal.

5. The method of claim 4, wherein performing the adaptive filtering operation comprises performing at least one of an affine projection operation and a least squares operation.

6. The method of claim 1, wherein generating the ECG signal comprises generating an anterior ECG signal from an anterior subportion of the array of electrodes and a posterior ECG signal from a posterior subportion of the array of electrodes, and wherein generating the de-noised ECG signal comprises:
   segmenting the anterior ECG signal into a first set of segments;
   segmenting the posterior ECG signal into a second set of segments;
   performing a quality assessment operation on the first set of segments and the second set of segments; and
   generating the de-noised ECG signal upon stitching segments of the first and the second sets of segments that satisfy a quality condition of the quality assessment operation.

7. The method of claim 1, wherein the array of electrodes is distributed across a conductive surface of a weighing scale, and wherein the method further comprises generating a weight distribution signal of the user from forces induced at the conductive surface, contemporaneously with generating the ECG signal from the array of electrodes at the conductive surface.

8. The method of claim 1, further comprising extracting, from the array of electrodes, an impedance plethysmography signal.

9. A method for electrical signal processing comprising:
   generating, from an array of electrodes distributed across a plane:
      electrical signals from a first left subportion and a first right subportion of the array of electrodes, the electrical signals comprising at least one of an electrocardiogram (ECG) signal and an impedance plethysmogram (IPG) signal;
      a noise signal from at least one of a second left subportion and a second right subportion of the array of electrodes, wherein generating the noise signal comprises generating a first noise signal from a left anterior electrode and a left posterior electrode of the second left subportion and a second noise signal from a right anterior electrode and a right posterior electrode of the second right subportion;
   generating a de-noised electrical signal upon isolating the noise signal from the electrical signals.

10. The method of claim 9, wherein the first left subportion and the second left subportion share at least one of a left anterior electrode and a left posterior electrode, and wherein the first right subportion and the second right subportion share at least one of a right anterior electrode and a right posterior electrode.

11. The method of claim 9, wherein generating the electrical signals comprises generating an anterior electrical signal from a left anterior electrode of the first left subportion and a right anterior electrode of the first right subportion and a posterior electrical signal from a left posterior electrode of the first left subportion and a right posterior electrode of the first right subportion.

12. The method of claim 11, wherein generating the de-noised electrical signal comprises:
   segmenting the anterior electrical signal into a first set of segments;
   segmenting the posterior electrical signal into a second set of segments;

performing a quality assessment operation on the first set of segments and the second set of segments; and generating the de-noised electrical signal upon stitching segments of the first and the second sets of segments that satisfy a quality condition of the quality assessment operation.

13. The method of claim 9, wherein generating the de-noised electrical signal comprises performing an adaptive filtering operation on the ECG signal and a summation of the first noise signal and the second noise signal, wherein the adaptive filtering operation comprises at least one of an affine projection operation and a least squares operation.

14. A system for electrical signal processing comprising:
a substrate;
an array of electrodes coupled to the substrate, wherein the array of electrodes comprises a left subportion and a right subportion, and wherein the left subportion comprises a left anterior electrode and a left posterior electrode, and the right subportion comprises a right anterior electrode and a right posterior electrode;
an electronics subsystem in communication with the array of electrodes; and
a computing subsystem comprising components of the electronics subsystem and comprising a non transitory computer-readable storage medium containing computer program code for:
generating electrical signals, comprising at least one of an electrocardiogram (ECG) signal and an impedance plethysmogram (IPG) signal, from the left subportion and the right subportion of the array of electrodes, the left subportion of electrodes and the right subportion of electrodes forming, during use, a circuit across an inferior sagittal plane of a user,
generating a first noise signal from the left subportion and a second noise signal from the right subportion of the array of electrodes, wherein generating the first noise signal comprises generating the first noise signal from the left anterior electrode and the left posterior electrode of the left subportion, and wherein generating the second noise signal comprises generating the second noise signal from the right anterior electrode and the right posterior electrode of the right subportion, and
generating a de-noised ECG signal upon processing the electrical signals with the first and the second noise signals.

15. The system of claim 14, wherein the array of electrodes comprises a conductive polymer electromechanically coupled to the substrate.

16. The system of claim 14, wherein the electronics subsystem comprises architecture comprising a first ECG channel coupled to the left anterior electrode and the right anterior electrode, a second ECG channel coupled to the left posterior electrode and the right posterior electrode, and a summation circuit for the first noise signal and the second noise signal.

* * * * *